United States Patent [19]

Hendrix et al.

[11] Patent Number: 5,247,558
[45] Date of Patent: Sep. 21, 1993

[54] X-RAY PARTICLE SIZE ANALYZER

[75] Inventors: Warren P. Hendrix; James P. Olivier, both of Lawrenceville; Jack J. Wagner; Clyde Orr, Jr., both of Dunwoody, all of Ga.

[73] Assignee: Micromeritics Instrument Corporation, Norcross, Ga.

[21] Appl. No.: 263,047

[22] Filed: Oct. 26, 1988

Related U.S. Application Data

[63] Continuation-in-part of Ser. No. 125,395, Nov. 25, 1987, Pat. No. 4,920,550, which is a continuation-in-part of Ser. No. 115,499, Oct. 30, 1987, Pat. No. 4,853,551.

[51] Int. Cl.$^5$ .............................................. G01N 23/06
[52] U.S. Cl. ...................... 378/51; 356/246; 356/441
[58] Field of Search ............ 378/51, 54, 55, 57; 356/246, 436, 440–442, 335, 336; 250/576, 573

[56] References Cited

U.S. PATENT DOCUMENTS

| 3,449,567 | 6/1969 | Olivier et al. | 378/51 |
| 3,621,243 | 11/1971 | Olivier et al. | 378/51 |
| 3,839,642 | 10/1974 | Shinnar | 356/335 |
| 4,282,745 | 8/1987 | Burr | 378/51 |
| 4,853,551 | 8/1989 | Wagner et al. | 250/515.1 |
| 4,920,550 | 4/1990 | Olivier et al. | 378/51 |

Primary Examiner—David P. Porta
Attorney, Agent, or Firm—Jones & Askew

[57] ABSTRACT

An x-ray sedimentation particle size analyzer in which data is taken only at particular positions along the sedimentation cell, and each such position is individually calibrated. Presentation of the data in the form of a particle size distribution curve can be accomplished very accurately using interpolation techniques. The sedimentation cell design is free of the effects of undesirable density gradients, capable of detecting and removing bubbles, capable of attaining a highly uniform dispersion of sample prior to sedimentation, and including a safety interlock device for blocking x-ray projection when the cell is being accessed.

4 Claims, 22 Drawing Sheets

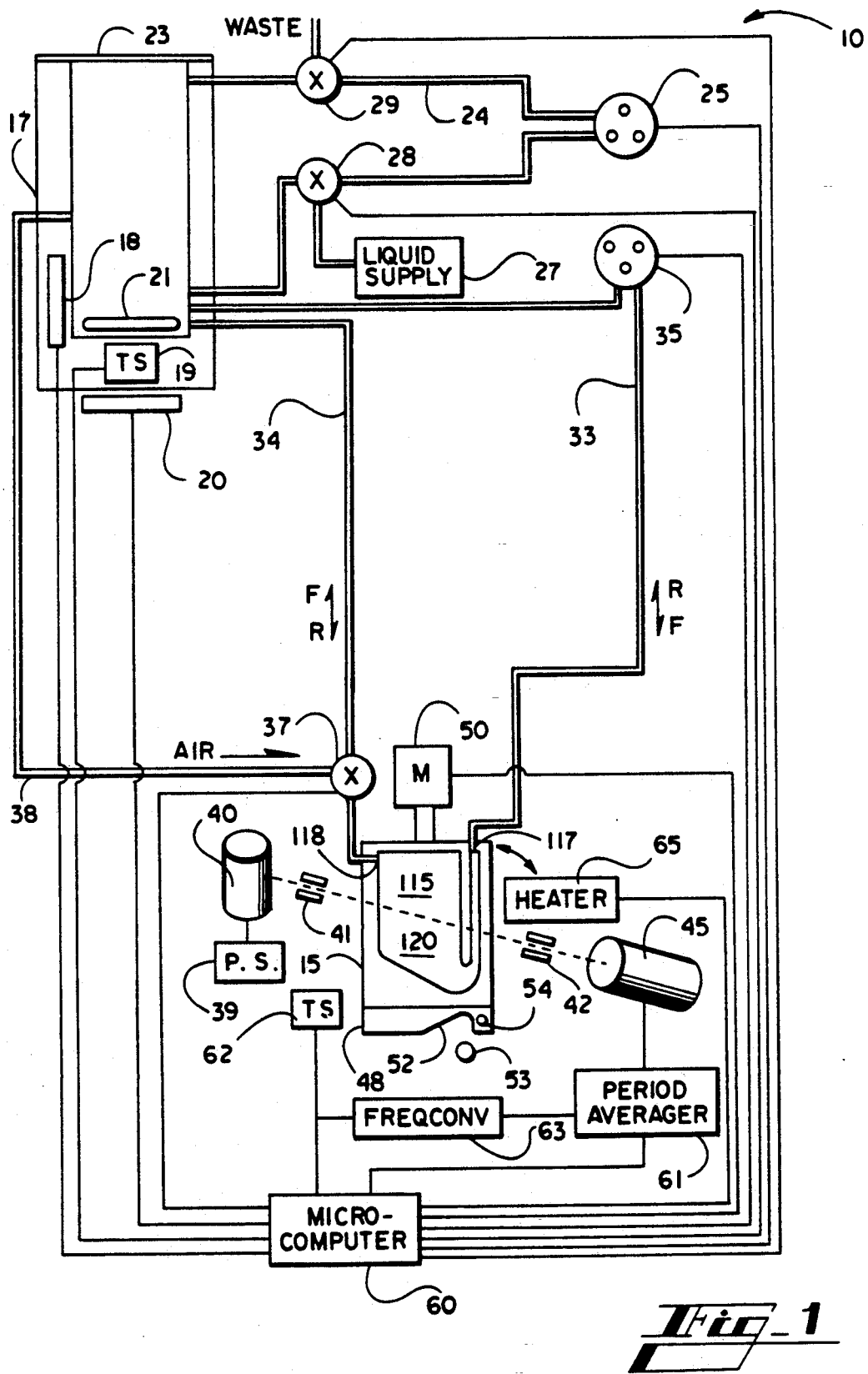
Fig_1

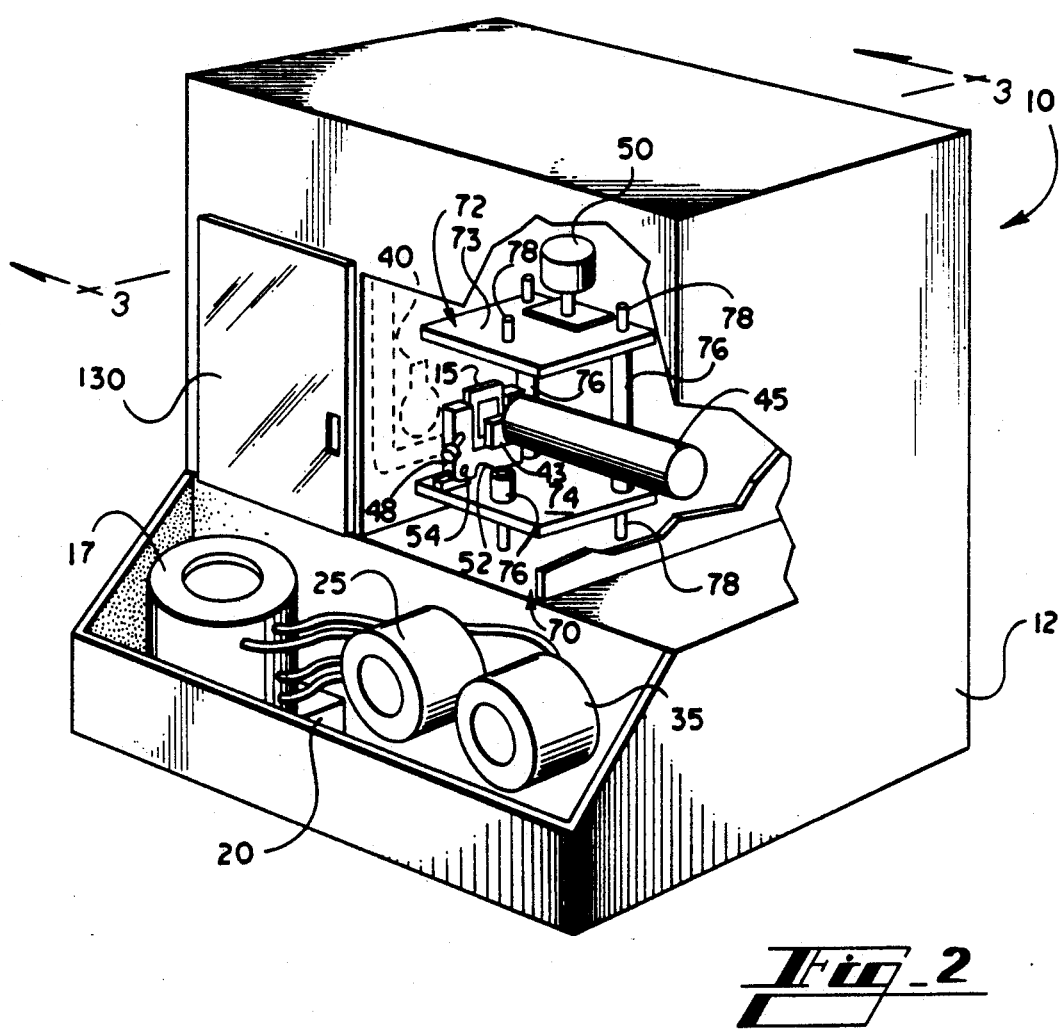
FIG_2

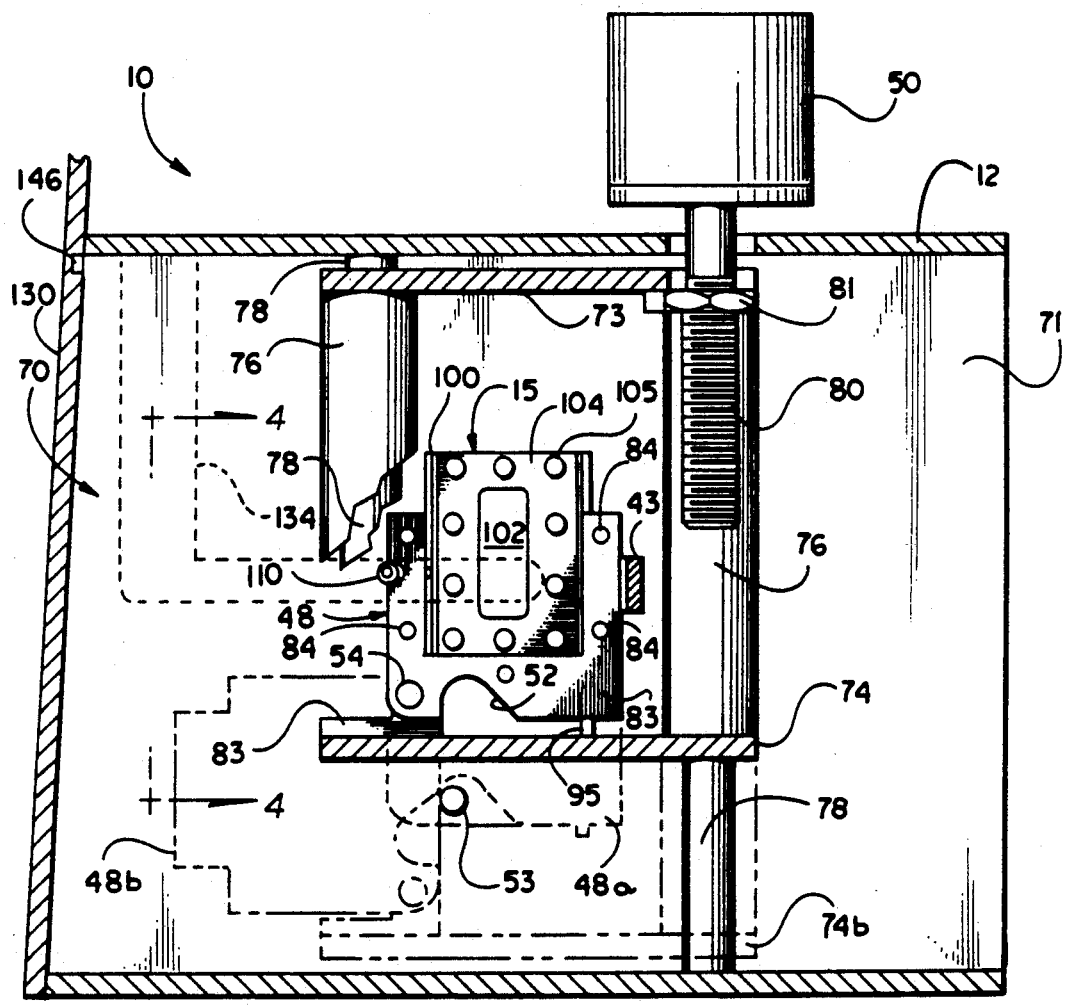
Fig_3

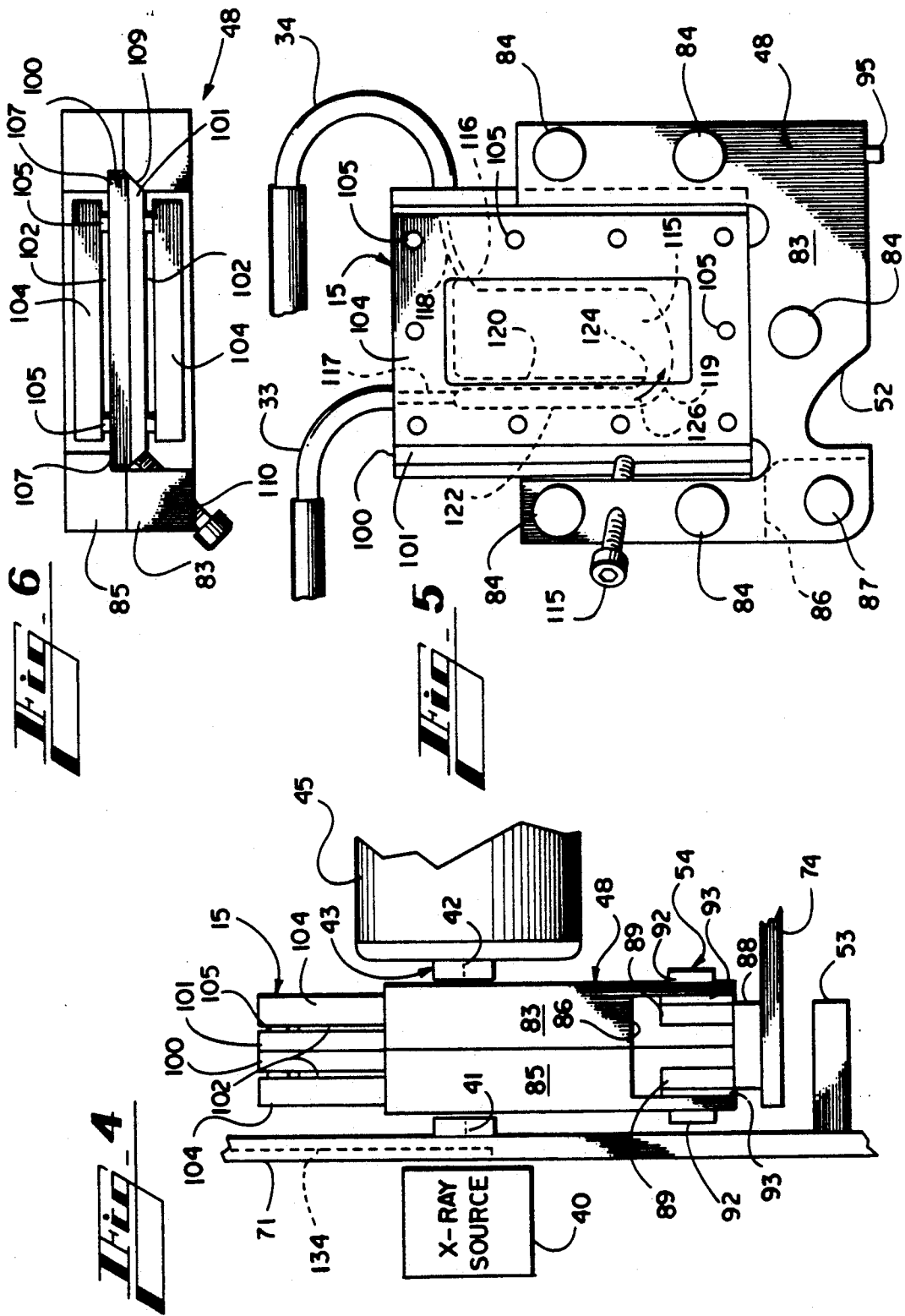

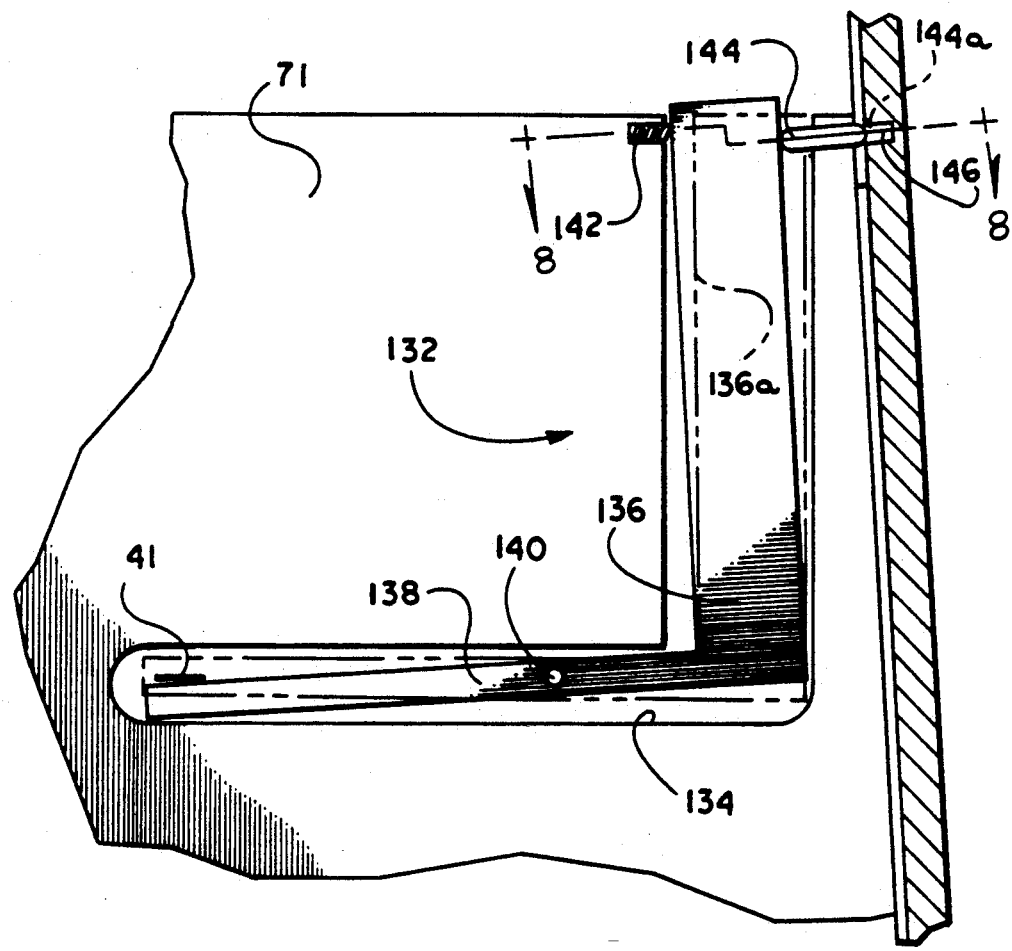
FIG_7
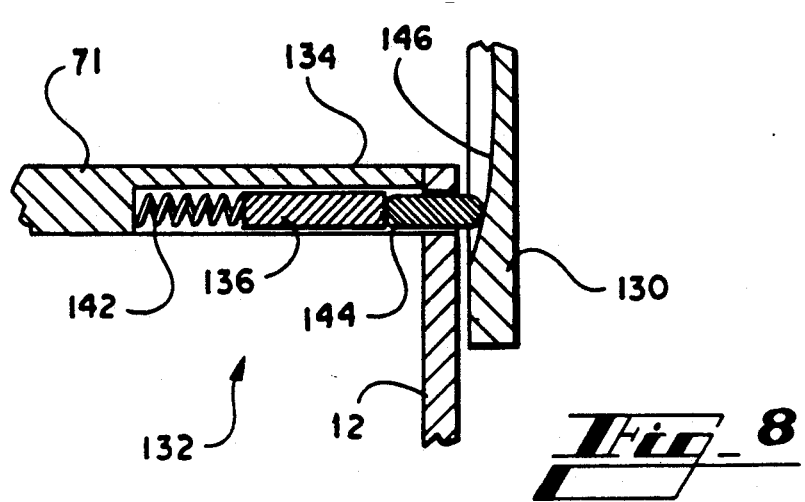
FIG_8

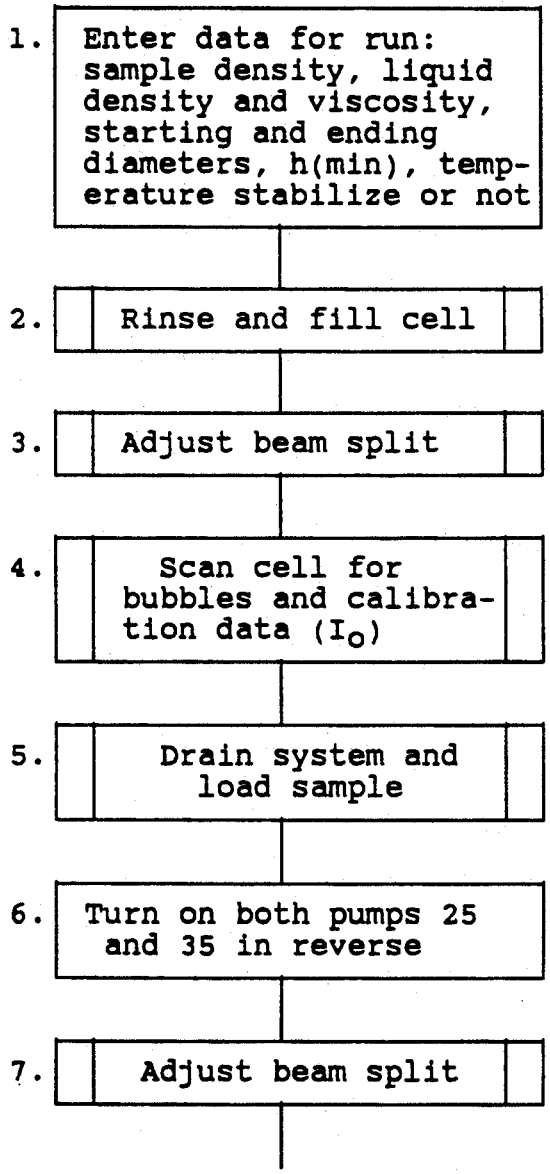
TO FIG. 9B
Fig_9A

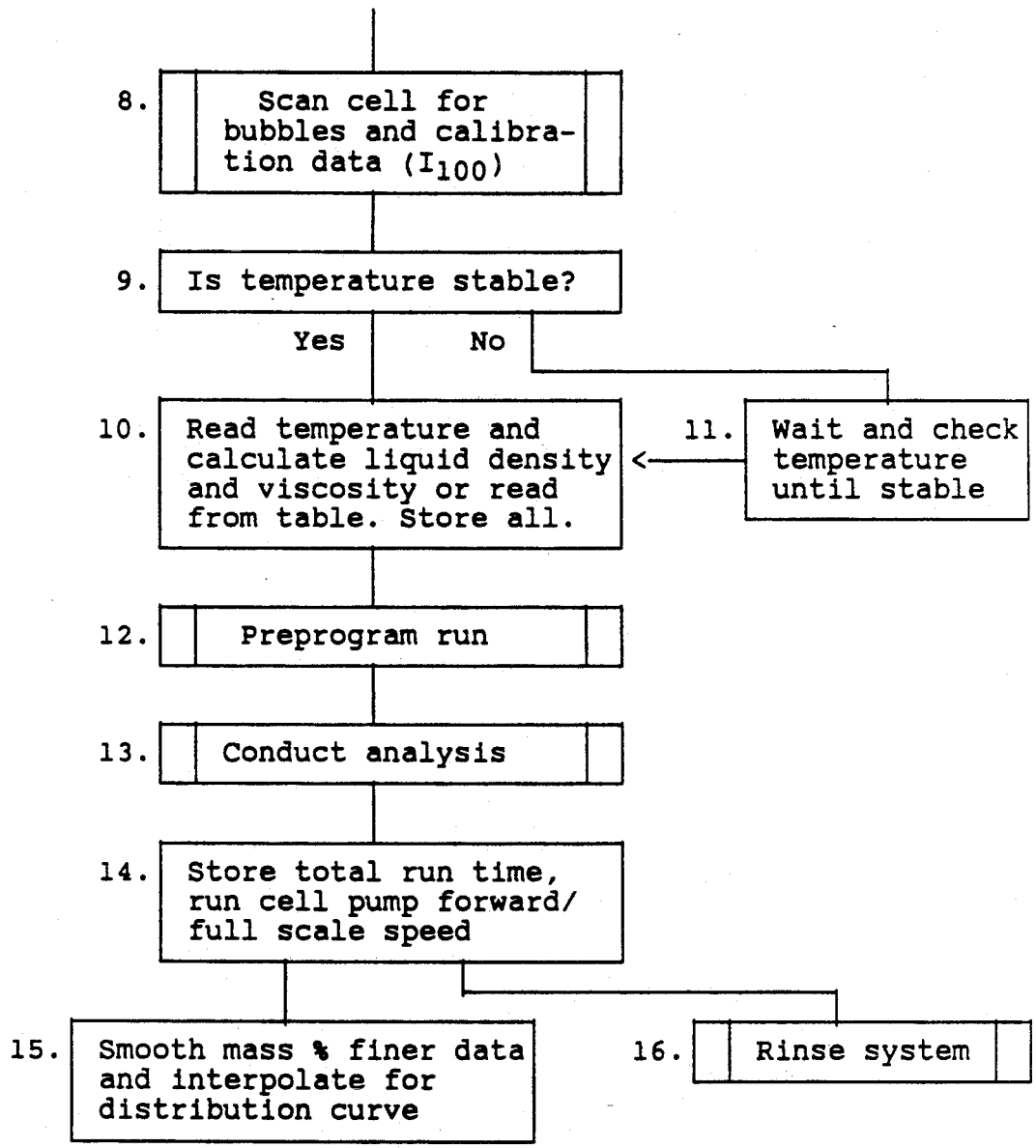
Fig_9B

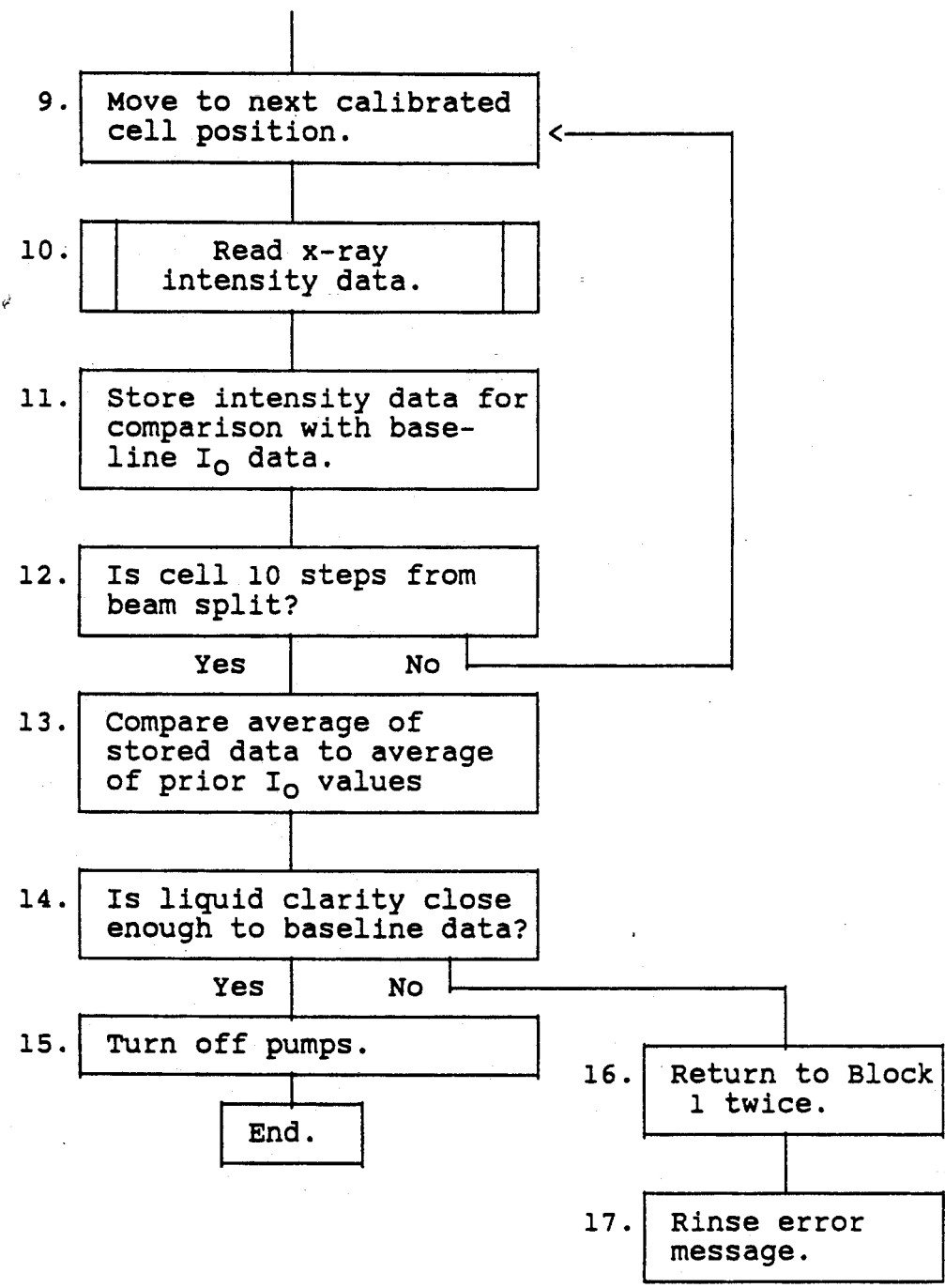
Fig_10B

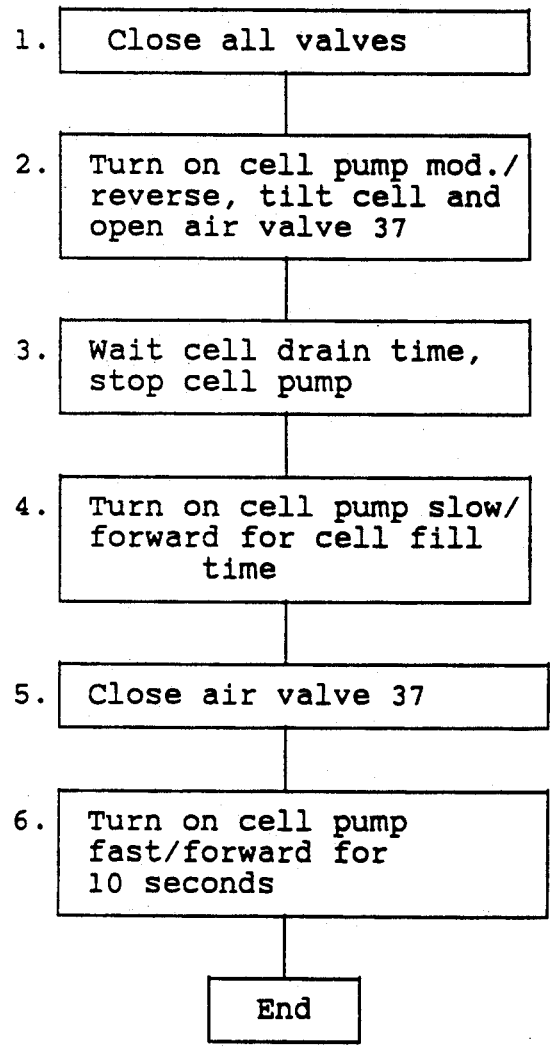
Fig_13

1. Close supply valve 27 and turn on mixer pump 25
2. Tilt cell and open waste and air valves 29 and 37
3. Turn on cell pump medium/reverse and wait for system drain time
4. Close waste and air valves 29 and 37 and stop both pumps
5. Add sample to mixing vessel and enter load go-ahead
6. Turn on mixer pump 25 and wait for mixer circulation time
7. Open air valve 37
8. Turn on cell pump 35 slow forward and wait for cell fill time
9. Close air valve 37 and turn on cell pump forward/fast for 10 secs.
10. Turn cell pump 35 to fast/reverse
11. Check concentration End Fig_14

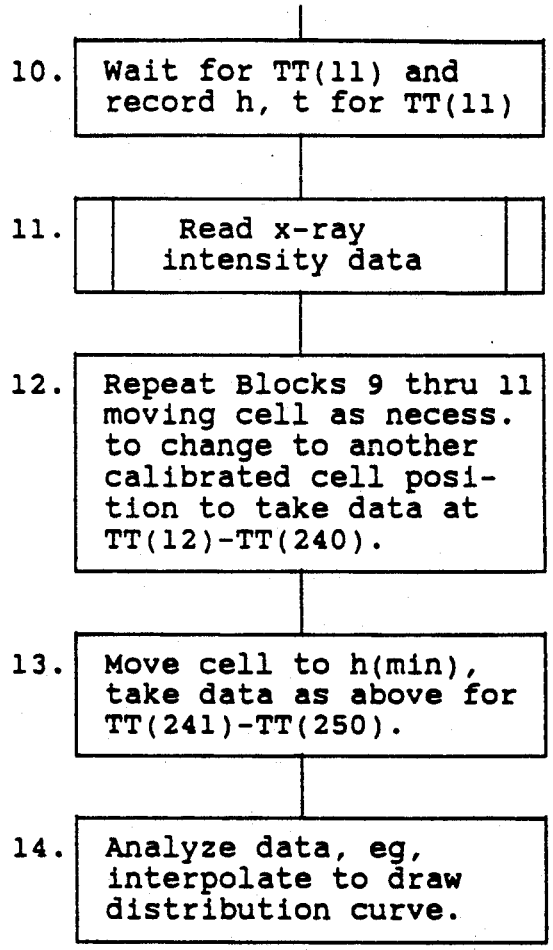
Fig_17B

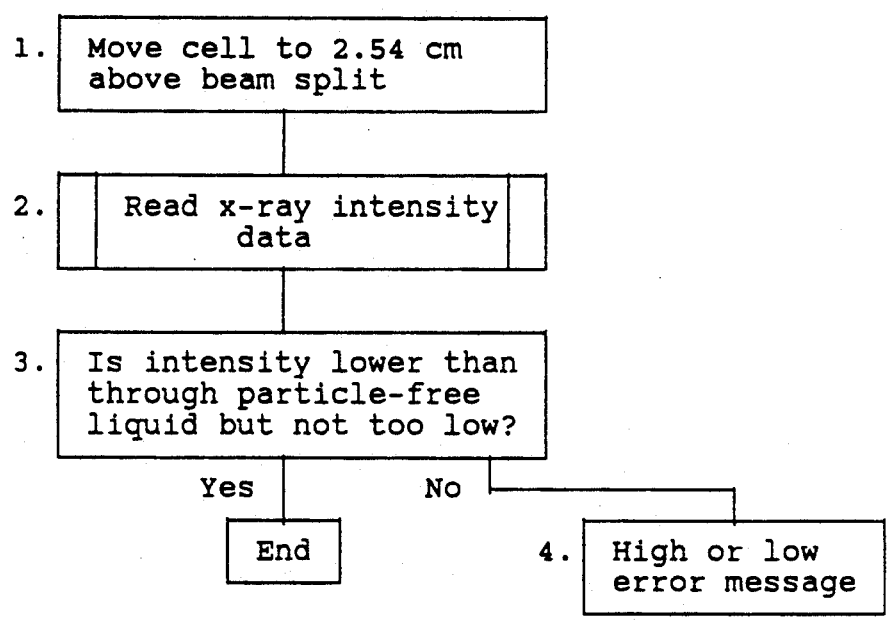
Fig_18

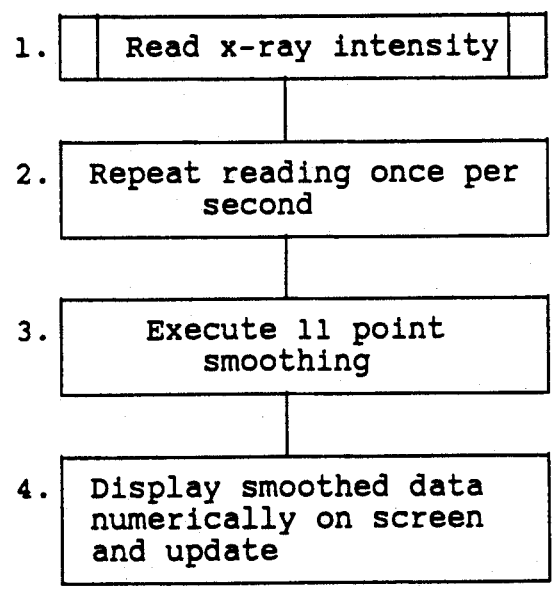
Fig_19

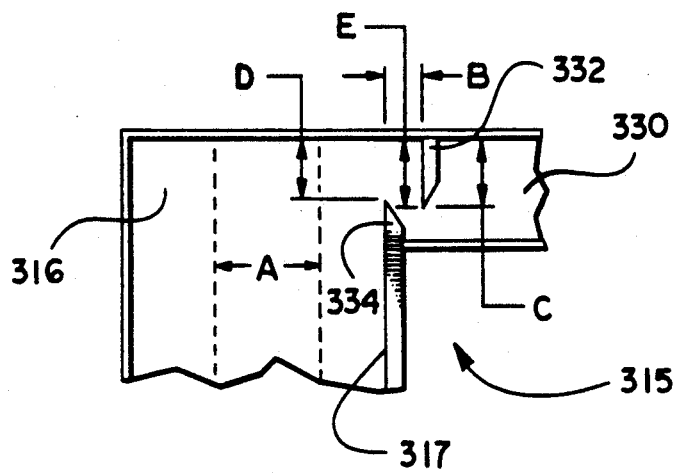
Fig_20
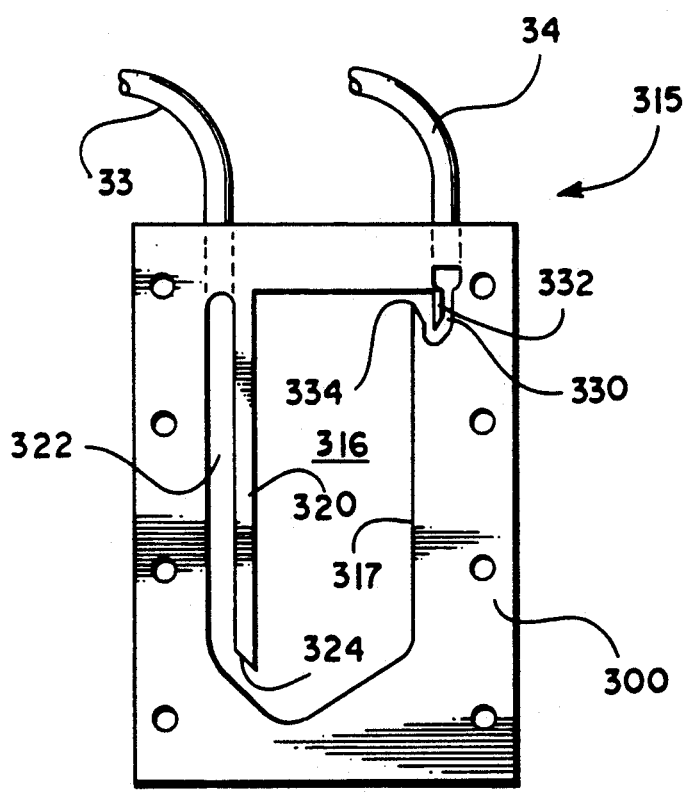
Fig_21

X-RAY PARTICLE SIZE ANALYZER

CROSS-REFERENCE TO RELATED APPLICATIONS

This application is a continuation-in-part of Ser. No. 125,395, filed Nov. 25, 1987, now U.S. Pat. No. 4,920,550 which is a continuation-in-part of Ser. No. 115,499, filed Oct. 30, 1987, now U.S. Pat. No. 4,853,551.

TECHNICAL FIELD

The present invention relates to particle size analysis using Stokes' Law sedimentation techniques and x-ray absorption, and more particularly relates to such analysis in which the relative position of the x-ray beam and sample cell is changed during analysis.

BACKGROUND ART

When using finely divided solids in industrial and scientific applications, it is often necessary to determine the distribution of the sizes of particles making up the sample. It may be critical, for example, that a catalyst be made up of particles at least a certain percentage of which by weight are smaller than a certain diameter. A typical manner in which particle size information is presented is the particle size distribution curve, which plots percent finer against particle size.

One widely used technique for determining particle size data uses Stokes' Law of sedimentation, which provides that at a given time after sedimentation of the sample suspended in a liquid has begun, particles larger than a given size will have fallen below a certain distance from the surface of the suspension. It follows that the percent of particles finer than the given size can be determined from the concentration of all particles at the certain distance. The transmission of x-rays through the suspension is a function only of the weight concentration of suspend solids, and therefore has provided the most convenient and accurate way to measure concentration in carrying out the sedimentation technique. Devices have been made using other electromagnetic radiation, such as visible light.

Significant economy in the time required for such an analysis was realized with the concept of continuously moving the sample cell and radiation source relative to one another during sedimentation while moving a pen plotting the particle size axis of the particle size distribution curve in a coordinated fashion to at all times satisfy Stokes' Law. This concept was disclosed in the early work of Muta, U.S. Pat. No. 3,315,066 and of Kalshoven, British Patent No. 1,158,338. Subsequent improvements disclosed in U.S. Pat. Nos. 3,449,567 and 3,621,243 to Olivier and Hickin led to successful commercial embodiments among them the Sedigraph 5000 series of instruments manufactured by Micromeritics Instrument Corporation. Detailed theoretical descriptions of the implementation of Stokes' Law in scanning x-ray particle size analyzers may be found in the patents listed above.

The length of time required for an analysis providing data for small particles sizes, e.g., down to 0.1 micron, has remained a problem with such instruments. In prior instruments, the cell must be moved very slowly in order to position it in a timely manner to record accurate data for the continuum of cell positions near the top of the cell. Run times of many hours, depending upon the nature of the sample and the suspending liquid, are the result. Furthermore, the distribution curve must be generated over the same length of time, even if an operator needs only a lower level of precision.

Sample cells for use with sedimentation particle size analyzers are designed to attempt to provide minimum distortion of the x-ray beam by the cell, to provide a bubble-free x-ray path, and to provide maximum dispersion of the sample in the liquid. A problem experienced with current analyzers has been difficulty in obtaining uniform dispersion of sample particles in the suspension prior to the beginning of sedimentation. Sample cells are typically connected via tubing to a mixing chamber, from which the suspension is pumped to the cell. Recirculation of the suspension through the cell and the mixing chamber has been relied upon to maintain a uniform suspension. However, because of interior cell geometry and the location of ports to which the tubing is attached, it has been found that areas of the cell often are not adequately swept by the flow of fluid, and therefore experience some premature settling of larger particles. The problem of settling may occur at the very top of prior closed top cells even when the cell pump is rapidly circulating the suspension. If the liquid's direction of travel is horizontally along the top wall, sedimentation can occur. This can result in an analysis indicating that the sample is finer than it is in fact.

Another problem has been lack of precise reproducibility of the results obtained for the same sample, particularly from machine to machine of the same type. Some relief of this problem was obtained by clamping off the supply tubing to the cell during analysis, and by randomly tilting the apparatus slightly on a trial-and-error basis until an orientation producing more consisting results was found. It is now suspected that the input and output tubing connected to the cell provides horizontal settling channels in which a density gradient can be created. The lighter portion of the suspension at the top of the tubing would have a tendency to rise, and could rise to the top of the cell itself. The presence of less dense material at the top of the cell not resulting from sedimentation in the cell itself would skew the observations taken in the region.

This problem is not as significant in cells which have both inlet and outlet at the top of the cell. However, it is important to have a port at the bottom of the cell to provide better flushing action for the removal of sedimentation deposits.

The introduction of closed-top cells facilitated accurate analysis of very small particles by eliminating the meniscus at the top of the suspension volume and thereby allowing precise determination of the sedimentation height. However, the closed cell created a greater likelihood that bubbles rising to the top of the cell would become trapped in the path of the x-ray beam. Such bubbles falsely reduced the apparent density of the suspension measured by the x-rays, and were quite capable of rendering an analysis useless. As they often were not detected except in the form of obviously flawed output, such bubbles often resulted in the waste of many hours required to re-run the sample.

In prior x-ray particle size analyzers, it is important that the x-ray path through the cell be uniform along the entire scanned height of the cell. The measured transmission of x-rays during a run is used to calculate "percent finer" according to the following equation:

$$\text{Percent finer} = \frac{\ln(I_x/I_o)}{\ln(I_{100}/I_o)},$$

where $I_o$ is the transmitted intensity through the cell containing only the suspending fluid, $I_{100}$ is the transmitted intensity through the cell containing the sample fully suspended before sedimentation, and $I_x$ is the measured transmitted intensity at a height and time during a run. Calibration of the cell requires a determination of $I_o$ and $I_{100}$. If the effect of the cell on the x-rays along the height of the cell is not uniform, $I_o$ and $I_{100}$ will not have a constant value for all measuring heights.

In prior analyzers, the construction of the cell has been made to fine tolerances in order to attempt to provide clear windows mounted in exactly parallel relationship to one another. These attempts have not been entirely successful. Furthermore, the cell windows can become dirty in a non-uniform manner, adding to the problem. Some prior analyzers have made a single measurement of $I_o$ and of $I_{100}$ at a selected cell height, and assumed that the cell is sufficiently uniform. Another technique has been to measure $I_o$ and $I_{100}$ at several heights and to accept the average of these measurements as representative of the cell for all calculations of percent finer. All such techniques result in somewhat inaccurate particle size results if there is a significant difference in cell transmission characteristics at different heights along the cell.

Thus, there has been a need in the art for an x-ray particle size analyzer capable of faster analysis, capable of highly uniform dispersion of the sample prior to sedimentation, not affected by sedimentation in tubing, capable of detecting and eliminating bubbles before the start of a run, and capable of compensating in a meaningful way for non-uniformities in x-ray transmission by the cell.

SUMMARY OF THE INVENTION

The present invention provides a number of novel concepts which solve the above-described problems in prior art x-ray particle size analyzers. An analyzer embodying the present invention provides more accurate, reproducible results, and can provide very rapid analysis when desired. The advantages of the invention follow in part from an abandonment of prior accepted practice of taking transmission data continuously at all cell heights and assigning calibration parameters to the cell as a whole. According to the invention, data is taken only at particular positions along the cell, and each such positions is individually calibrated. Presentation of the data in the form of a particle size distribution curve can be accomplished very accurately using interpolation techniques. Other features of the invention include a cell design free of the effects of undesirable density gradients, capable of detecting and removing bubbles, capable of attaining a highly uniform dispersion of sample prior to sedimentation, and including a safety interlock device for blocking x-ray projection when the cell is being accessed.

Generally described, the present invention provides an apparatus and method for acquiring information relating to the distribution of particle sizes in a sample undergoing sedimentation in a suspension of the sample in a fluid medium contained in a sample cell, while passing a photon beam, preferably x-rays, from a radiation source through the suspension of the sample, by moving either the cell or the source to aim the x-ray beam at a first predetermined location along the cell; waiting at the predetermined location until one or more selected times after the beginning of sedimentation; and measuring and recording the transmitted intensity of x-rays through the cell containing the suspension at the one or more selected times. Operation can continue by moving either the cell or the x-ray source to aim the x-ray beam at a second predetermined location along the cell spaced apart from the first predetermined location; waiting at the second predetermined location until an additional one or more selected times after the beginning of sedimentation; and measuring and recording the transmitted intensity of x-rays through the suspension at the one or more selected times. The procedure can be repeated until information has been obtained over a desired range of particle sizes, and a particle size distribution curve can be produced by interpolation between information obtained at the selected times.

The invention also provides a sample cell apparatus for use in a sedimentation particle size analyzer, comprising a sample compartment and a fluid passageway adjacent to one side of the compartment, extending downwardly to enter the side of the compartment from an angle above the horizontal, such that the passageway provides essentially no horizontal settling channel from which low density material can rise to the top of the compartment. This result can also be accomplished by having the passageway deliver fluid vertically downwardly into the compartment. The passageway preferably extends from a height above the bottom of the compartment to discharge fluid into the compartment at the bottom of the compartment, and preferably extends downwardly from a height at or above the top of the compartment.

In the preferred embodiment, the sample compartment and fluid passageway are defined within a chamber by a vertical wall extending from the top of the chamber to a point spaced downwardly from the top of the chamber, the wall being tapered at its bottom end to provide angled entry into the sample compartment portion of the chamber.

A capability for cleaning the cell and removing any bubbles can be provided by including means for tilting the compartment in the direction of the passageway and draining the contents of the compartment through the passageway while venting the compartment through a port at the top of the compartment, and means for filling the compartment through the passageway while the compartment is tilted by reversing the cell pump and venting gas from the compartment through the port. To detect and eliminate bubbles automatically, the apparatus can include means for detecting and eliminating bubbles from the compartment, comprising means for measuring the transmission of electromagnetic radiation through the compartment at a plurality of locations along the height of the compartment; means for determining the degree of uniformity of the transmission among the locations; and means responsive to the uniformity determining means for operating the tilting, draining and filling means to re-fill the compartment.

The port at the top of the compartment is oriented to allow fluid to be injected very rapidly along the top surface of the compartment. A more uniform suspension results because the suspension at the top of the cell is replaced before any significant sedimentation can occur. Since the suspension is more uniform very close to the top of the cell, the x-ray beam can be moved closer to the top of the cell, and this permits faster runs without sacrificing accuracy. The use of a reversible, multi-speed cell pump enables this rapid circulation in one direction as well as the slow filling of the cell in the other direction to eliminate bubbles, as described above.

The invention also provides a safety interlock device for a cabinet containing an x-ray source and having a door for providing access to the interior of the cabinet, comprising a plate mounted for pivotal movement about an axis from a blocking position in which the plate prevents x-rays from entering the cabinet to a clear position in which the plate is out of the path of the x-rays; an arm extending from a location on the plate on the opposite side of the axis from the x-ray source; and cam means movable with the door and engaging the arm for moving the plate from the blocking position to the clear position responsive to closing of the door. The device can also include means for urging the plate into the blocking position, and the center of gravity of the plate and arm is preferably spaced apart from the axis, such that the plate normally pivots into the blocking position.

Thus, it is an object of the present invention to provide an improved sedimentation particle size analyzer.

It is a further object of the present invention to provide a sedimentation particle size analyzer which conducts rapid automatic analyses.

It is a further object of the present invention to provide a sedimentation particle size analyzer which compensates for non-uniformities in cell optics.

It is a further object of the present invention to provide a sedimentation particle size analyzer which disperses a sample into a highly uniform suspension prior to sedimentation.

It is a further object of the present invention to provide a sedimentation particle size analyzer which is not affected by density gradients formed in tubing or other settling channels.

It is a further object of the present invention to provide a sedimentation particle size analyzer which collects data in a manner which allows flexible presentation of the analytical results.

It is a further object of the present invention to provide a sedimentation particle size analyzer which detects and eliminates bubbles in the sample cell.

It is a further object of the present invention to provide a sedimentation particle size analyzer which gives highly reproducible results from run to run and from machine to machine.

It is a further object of the present invention to provide an improved sample cell for a sedimentation particle size analyzer.

It is a further object of the present invention to provide a sample cell for a sedimentation particle size analyzer having improved capabilities for draining, filling and debubbling, and which is not subject to problems caused by density gradients in tubing or other settling channels.

It is a further object of the present invention to provide an improved x-ray safety interlock for a sedimentation particle size analyzer.

Other objects, features, and advantages of the present invention will become apparent upon reading the following detailed description of embodiments of the invention, when taken in conjunction with the accompanying drawing and the appended claims.

BRIEF DESCRIPTION OF THE DRAWING

FIG. 1 is a schematic representation of an x-ray particle size analyzer embodying the present invention.

FIG. 2 is a pictorial view of the particle size analyzer with portions broken away to show interior detail.

FIG. 3 is a partial vertical cross sectional view taken along line 3—3 of FIG. 2, showing positions of the movable cell.

FIG. 4 is a partial front plan view of the analyzer taken along line 4—4 of FIG. 3.

FIG. 5 is a side plan view of the cell assembly and cell mounting block.

FIG. 6 is a top plan view of the cell and mounting block of FIG. 5.

FIG. 7 is a side plan view of the safety interlock device of the present invention.

FIG. 8 is a horizontal cross sectional view taken along line 8—8 of FIG. 7.

FIGS. 9A and 9B are a schematic flow diagram of the overall operation of the particle size analyzer.

FIGS. 10A and 10B are a schematic flow diagram of the cell rinse and fill sequence utilized in operation of the present invention.

FIG. 13 is a schematic flow diagram of the sequence for draining and refilling the cell utilized in operation of the present invention.

FIG. 14 is a schematic flow diagram of the cell drain and load sequence utilized in operation of the present invention.

FIGS. 17A and 17B are a schematic flow diagram of the sequence for conducting an analysis of a sample utilized in operation of the present invention.

FIG. 18 is a schematic flow diagram of the sequence for checking sample concentration utilized in operation of the present invention.

FIG. 19 is a schematic flow diagram of the sequence for displaying current x-ray intensity data utilized in operation of the present invention.

FIG. 20 is a diagrammatic representation of a modified sample cell profile embodying the invention.

FIG. 21 is a side plan view of a cell cavity construction utilizing the concepts shown in FIG. 20.

DETAILED DESCRIPTION

Figure 10A:
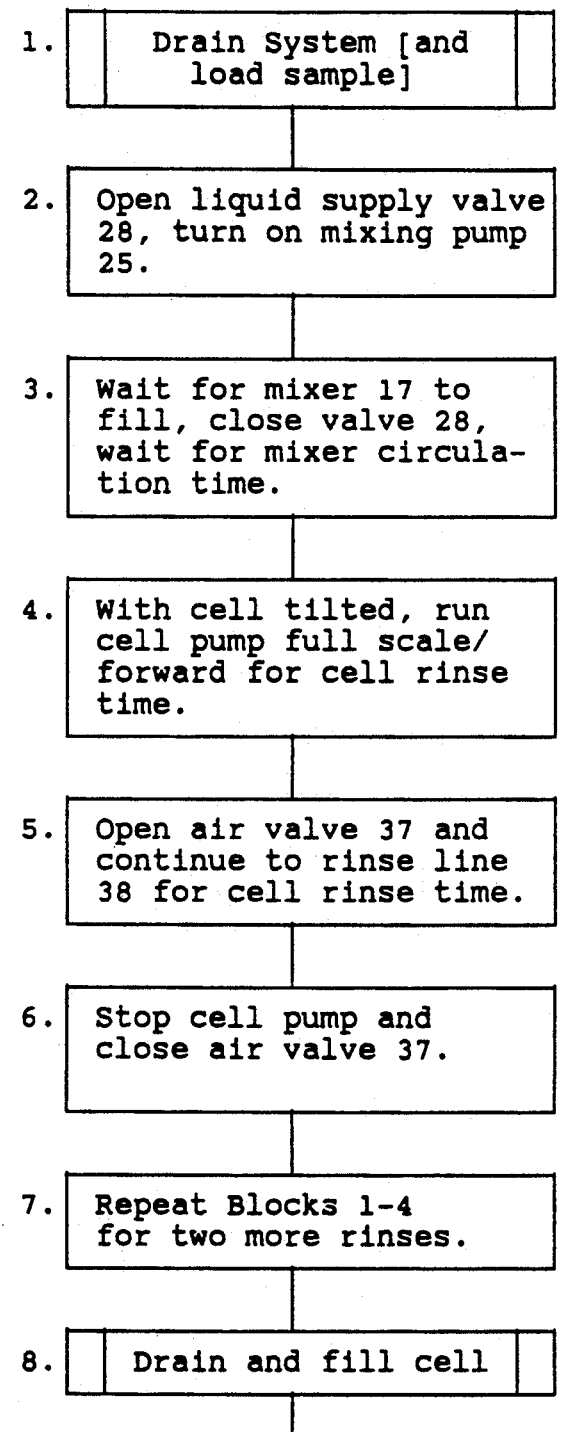

Referring now to the drawing, in which like numerals refer to like parts throughout the several views, FIG. 1 shows a schematic representation of a sedimentation particle size analyzer 10 embodying the present invention. FIG. 2 is a pictorial view of a preferred embodiment of the analyzer 10, which is preferably contained in a housing 12. Sedimentation of sample particles suspended in a liquid takes place in a sample cell 15. The sample and liquid are mixed together in a temperature controlled mixing vessel or chamber 17 by a variable speed magnetic stirrer 20 positioned below the mixing vessel 17. The stirrer 20 rotates a stirrer element 21 positioned within the vessel 17 to thoroughly mix the contents of the vessel.

The contents of the mixing vessel can also be recirculated through a recirculation line 24 which includes a mixing pump 25. Operation of the stirrer 20 is preferably controlled concurrently with operation of the mixing pump 25, which can be a uni-directional peristaltic pump. The line 24 includes a liquid inlet valve 28 through which liquid can be drawn from a liquid supply reservoir 27. The line 24 also includes a waste valve 29 through which the contents of the mixing chamber 17 may be routed to waste. In the preferred embodiment, the reservoir 27 and supply valve 28 are located upstream of the pump 25, and the waste valve 29 is located downstream of the pump 25.

The mixing vessel 17 is maintained at a temperature adjustable by the operator within a range, preferably 20-50 degrees C., by means of a resistance heater 18 embedded in the wall of the vessel. With input from a temperature sensor 19 positioned beneath the vessel, a conventional analog DC proportional controller maintains the temperature set by the operator within plus or minus 0.5 degree.

The cell 15 is connected to the mixing vessel 17 by two supply lines 33 and 34. The line 33 includes a reversible cell pump 35, preferably a peristaltic pump. Forward and reverse pump directions are shown by arrows F and R in FIG. 1. Operating in a forward direction, the pump 35 supplies liquid (sometimes containing suspended sample) from the vessel 17 to the cell 15, whereas in its reverse direction the pump returns liquid from the cell to the vessel through the line 33. When the cell is filled with fluid, further operation of the pump 35 in a forward direction forces fluid out of the cell into the line 34 and back to the vessel 17. Conversely, reverse operation of the pump 35 can draw fluid from the vessel 17 into the cell 15. The line 34 includes an air valve 37 which vents the line and the cell back to the vessel 17 through a fluid line 38.

Concentration of the suspension in the cell 15 during sedimentation is measured by passing x-rays from an x-ray source 40 through a first slit 41, the cell 15, and a second slit 42, after which the x-rays are detected by a conventional photodetector 45, such as a geiger counter or scintillator-photomultiplier tube combination. The slits are defined in a U-shaped yoke 43 which surrounds the cell on three sides, as shown in FIG. 2. The x-ray source 40 is powered by a highly regulated DC power supply 39 of a type known to those skilled in the art.

The cell 15 is mounted on a U-shaped cell mounting block 48 best shown in FIGS. 4-6 and described in detail below. The mounting block 48 is positioned for movement by a cell stepping motor 50. The cell moves up and down relative to the x-ray beam during analysis. Those skilled in the art will understand that this scanning of the x-ray beam can also be accomplished by moving the x-ray source rather than the cell. The present invention also provides a means for tilting the sample cell, which in the preferred embodiment occurs when the sample cell 15 is lowered by the motor 50 below the x-ray beam. A cam surface 52 defined in the bottom portion of the cell mounting block 48 engages a cam follower pin 53. The force of the cam surface on the pin 53 causes the mounting block 48 and cell 15 to tilt about a pivot axis 54, for purposes of filling, recirculating and bubble elimination as described below.

Operation of the sedimentation particle size analyzer 10 is controlled by a microcomputer 60, which can be a general purpose personal computer. Conventional interfaces are provided, preferably on a plug-in expansion board (not shown), to operate and monitor the stirrer 20, the pumps 25 and 35, the valves 28, 29 and 37, the cell motor 50, and a conventional temperature sensor 62 mounted near the cell. The computer is also interfaced with the photodetector 45 through a period averaging circuit 61, which reads the x-ray intensity data detected by the detector 45. The operation of the period averager 61, which may be placed on the same expansion board, is described below. Neither the temperature controllers nor the x-ray source 40 need be interfaced with the computer.

Referring now to FIG. 2, the housing 12 defines a temperature controlled cell compartment 70 in which is located an elevator assembly 72. The elevator 72 includes an upper plate 73 and a lower platform 74 held in spaced apart horizontal relation by three columns 76. The columns 76 are hollow and include interior bearings (not shown). Three guide rods 78 pass through the columns 76 and the plates 73 and 74. The guide rods are anchored in the housing 12 at their top and bottom ends. In FIG. 2, the anchor points of the top ends of the rods 78 are not shown.

A drive screw 80, shown in FIG. 3, extends downwardly from the motor 50, mounted above the cell compartment, through a drive nut 81 mounted in the upper plate 73 of the elevator unit 72. Rotation of the screw 80 causes the elevator to move up and down along the guide rods 78. The drive nut 81 and screw 80 are fitted with a conventional anti-backlash device designed to create a precise relationship between the degree of rotation of the screw 80 and the actual motion of the elevator, and therefore of the cell 15.

The cell compartment 70 is maintained at the same temperature as the mixing vessel 17 by a resistance heater 65 mounted at the back of the compartment. An air circulation fan (not shown) associated with the heater 65 helps to maintain uniformity of the temperature, which is controlled with input from the temperature sensor 62 by an analog DC proportional controller.

The cell 15 and mounting block 48 are shown in more detail in FIGS. 4-6. The mounting block 48 consists of two U-shaped halves, 83 and 85, connected by screws 84. When secured together, the halves define in the lower edge of the block 48 the cam surface 52. Also defined is a cavity 86 at the lower corner of the block 48 at which is located the pivot axis 54. A pair of openings 87 pass through the halves 83 and 85 of the block 48 along the pivot axis 54 to communicate with the cavity 86. An anchoring foot 88 is attached to the platform 74 adjacent to the front edge thereof and defines a pair of vertical arms 89 extending up into the cavity 86. A pair of bolts 92 extend from the exterior of the block 48 through the openings 87, through a pair of bearings 93, and are secured in the vertical arms 89. The mounting block 48 is thus pivotable about the bolts 92, which lie along the pivot axis 54. A stop 95 extends downwardly from the bottom surface of the block 48 spaced apart from the pivot axis 54, to engage the platform 74 and maintain the block 48 and cell 15 in a level condition when the cell is above the pin 53, as shown in FIG. 3.

Referring to FIGS. 5 and 6, the cell assembly 15 includes a central plate 100 which has beveled vertical edges 101 on one side and is cut out to define a cell cavity 115. The central plate is sandwiched by a pair of windows 102, of materials well known in the art, and further by a pair of clamping plates 104 which define central cut-outs to expose the portion of the windows covering the cell cavity 115. The assembly is held together by a plurality of screws 105.

The cell assembly 15 fits into the mounting block 48 as shown in FIGS. 5 and 6. The U-shaped half 83 of the block 48 defines a pair of flat shoulders 107 along the inside vertical edges of the "U". The other half 85 defines a beveled shoulder 109 along one of its inside edges, and a set screw 110 is tapped at an angle through the other arm of the "U". Thus, the assembled halves 83 and 85 form a pocket for matingly receiving one vertical side of the cell assembly 15 with one beveled edge 101 engaging the beveled shoulder 109, and the set screw being tightened against the other beveled edge 101. The cell 15 also sits firmly on the lower horizontal portion of the "U" of the block 48. Therefore, when the set screw 110 is tightened, the cell is in a well defined, reproducible position with respect to the rest of the analyzer 10.

The cell cavity 115 defined by the plate 100 has a unique cross sectional shape best shown in FIG. 5. The cavity is generally rectangular, and is connected to the line 33 at the upper corner of the cavity nearest to the pivot axis 54 by a passageway 117, and to the line 34 at the other upper corner by a passageway 118. A notch or recess 116 is formed in the wall of the cavity at the point of entry of the passageway 118. This notch 116 helps to prevent bubbles from collecting at the corner of the cavity. The passageways 117 and 118 may serve as either inlet or outlet passageways depending on the direction of operation of the cell pump 35. The lower corner 119 of the cavity 115 nearest to the pivot axis 54 is rounded. A vertical wall 120 extends downwardly from the top of the cavity 115 and terminates adjacent to the corner 119. The wall 120 is spaced apart a short distance from the side of the cavity to form a channel 122 through which fluid must travel between the main sedimentation compartment of the cavity and the passageway 117. The wall 120 is curved at its end 124 to match the curvature of the corner 119. Fluid entering the cavity 115 from the passageway 117 thus sweeps down the channel 122 and into the bottom of the cavity at a downward angle as shown by the arrow 126 in FIG. 5.

The structure of the cell cavity as just described allows fluid entry at both the top and bottom of the cell for circulation and flushing purposes, but provides virtually no horizontal settling channels in which density gradients might form and affect the density in the main compartment in which the analysis occurs. Because of the angled entry of the channel 122 into the main compartment, any lighter density suspension that does form at the end 124 of the wall 120 will tend to rise up the channel 122 rather than within the main compartment, and therefore will not disrupt the analysis. Prior to the analysis, rapid circulation entering through the upper passageway 118 replaces the suspension at the top of the cell so rapidly that no significant settling can occur. The analysis thus begins with a highly uniform suspension.

A unique safety interlock system 132 is provided in the analyzer 10 to prevent x-rays from entering the cell compartment 70 when access into the compartment 70 is possible. As shown in FIGS. 7 and 8, the cell compartment 70 is fitted with a sliding door 130, preferably made of a transparent plastic material. To provide the interlock, an L-shaped recess 134 is formed in the exterior surface of the side wall 71 of the cell compartment 70 which separates the compartment 70 from the x-ray source 40, as best shown in FIG. 4. An L-shaped rocker member 136 is mounted within the recess 134 to pivot about a pin 140 engaging a horizontal leg 138 of the rocker member 136. The pin 140 is positioned such that the center of gravity of the rocker member 136 is on the side of the pin closest to the door 130. Furthermore, a spring 142 is provided acting against the top of the rocker member 136 to force the rocker member toward the door. Such a position 136a is shown in dotted lines in FIG. 7, and it will be seen that the leg 138 covers the slit 41, preventing x-rays from passing through the slit into the compartment 70.

A plunger 144 is slidably fitted through the housing 12 so as to engage both the door 130 and the rocker member 136. The door 130 is provided with a recessed horizontal cam track 146 along which the plunger 144 travels as the door is opened and closed. As shown in FIG. 8, when the door is closed, the cam track pushes the plunger 144 inwardly against the rocker member 136 and pivots the leg 138 downwardly to its full line position in FIG. 7. This exposes the slit 41 and allows x-rays to pass through the cell 15. When the door is opened, the spring 142 and gravity acting on the rocker member 136 urge the plunger 144 into the cam track 146 (position 144a in FIG. 7), which becomes deep enough to allow the rocker member 136 to pivot to cover the slit 41.

The microcomputer 60 controls the various elements of the system during operation in a manner described below. In a conventional manner, the computer sets and resets bits on the interface expansion board to send signals to operate relays to switch valve positions, switch pumps on or off, and switch the direction and speed of the cell pump. Signals are similarly sent to the cell stepping motor controller to tell it which direction to move the cell, at what speed, and how many steps of the stepping motor 50 to move.

The period averager 61 receives the output from the photodetector 45, but ignores it except when instructed by the computer to read the output. The period averager includes a clock crystal and two counters. A signal is sent from the computer telling the period averager to count a certain number of x-ray photons and to send back the time elapsed during the counting process. One counter of the period averager counts the elapsed time and the other counts down from the predetermined number of x-ray pulses received. When the x-ray count reaches 0, a signal is generated shutting down the x-ray sampling, setting the clock count, and setting a status bit indicating that the task is complete. The computer may then calculate the elapsed period required for receipt of the x-ray data, which represents the transmitted intensity of x-rays through the suspension in the cell, and also the concentration of the sample.

The period averager also receives temperature data for purposes of displaying the current temperature measured by the temperature sensor 62. The signal from the sensor is converted to a voltage and then to a frequency by a frequency conversion circuit 63. The output of the circuit 63 is received by the period averager 61, which measures the reciprocal of the frequency and sends the computer elapsed time data. The computer converts the data to a temperature value that can be displayed on the screen of the computer. The foregoing circuitry performs conversions and calculations the implementation of which is well known to those skilled in the art.

The temperature sensor 62 is also directly connected to the interface expansion board where the signal from the sensor sets or resets a single bit depending upon whether the temperature is within plus or minus one-half degree of the operator-adjusted set point. This signal is used during the operation of the system to determine whether the temperature of the cell environment is stable prior to an analysis, as described below.

OPERATION

Operation of the sedimentation particle analyzer 10 is diagrammatically presented in the series of flow charts shown in FIGS. 9–18. In these flow charts, blocks having double side lines indicate an instruction to carry out a subroutine sequence shown in another drawing figure.

Generally, the cell is rinsed and filled with the liquid to be used to suspend the sample, such as water or organic liquid. Then the "beam split" position of the cell with respect to the x-ray beam is determined. This is the position at which the x-ray beam is directed precisely at the very top of the enclosed sample compartment 115, and is taken as the location at which the intensity of the x-ray beam is one-half of the intensity of the unobstructed beam passing through the cell windows. This position is stored as the reference point for determining precise cell locations during movement of the cell, as required for Stokes' Law calculations.

Subsequently, the cell containing particle-free suspending liquid is moved past the x-ray beam to obtain the $I_o$ baseline transmitted intensity data for a plurality of individual cell positions. Analysis data for generating an accurate particle size distribution will be taken only at these calibrated data acquisition positions. This scanning procedure is also carried out to determine whether bubbles are present in the cell, and, if so, to eliminate the bubbles by refilling the cell in a tilted orientation. Then the cell is drained and loaded with a suspension of the sample in the liquid. Information necessary for the analysis is input into the computer memory (or recalled from tables in the computer data storage) relating to the sample density, the liquid density and the liquid viscosity. Information is also input concerning the desired accuracy or resolution of the analysis, which affects the speed with which the analysis will be completed.

Meanwhile, the $I_{100}$ calibration data is being obtained by moving the cell containing the fully suspended sample to each of the positions for which $I_o$ was measured, and again measuring the x-ray transmitted intensity. Again, the scanning information is used to determine whether bubbles are present. If the cell transmittance is reasonably uniform, the temperature stability of the cell may be checked. When the temperature is stable, the computer executes a preprogramming routine to establish the cell positions and times at which data points will be taken. The analysis is commenced by turning off the cell pump 35 and allowing the sample to settle through the liquid. X-ray transmitted intensity is measured at many, but usually not all, of the calibrated cell positions. Several data points may be taken while the cell is stopped at one location. When 250 data points have been taken according to the preprogrammed schedule, the run time is recorded and the cell fluid circulated to resuspend the sediment. If appropriate, the cell is rinsed. Subsequently, the operator calls upon the computer to process the collected data and to prepare graphic or tabular representations of the particle size distribution and other characteristics of the sample.

ENTER RUN DATA

Describing the operation of the system in more detail, block 1 of FIG. 9 indicates the parameters and instructions the operator must input in order for the system to carry out an analysis. These are preferably input before the following procedures are carried out, but some are not actually needed until particular operations are conducted. The computer storage devices may be used to store tables of such data for "standard" samples and liquids, and also run parameters, that will be used repeatedly.

In order for the computer to use Stokes' Law, the sample density and the suspending liquid density and viscosity must be entered. If the density and viscosity data are input for three or more temperatures, the computer interpolates to provide data for the entire range between the extreme temperatures. Also needed are the starting and ending diameters the operator wishes to be analyzed, the minimum cell height with respect to the x-ray beam, and an instruction whether or not to delay the run for temperature stabilization. The purpose of these parameters will be described below as they are used.

RINSE

Block 2 of FIG. 9 refers to the "Rinse and fill cell" routine of FIG. 10. Block 1 of FIG. 10 refers to the "Drain system [and load sample]" routine of FIG. 14. The load sample portion of this routine is optional and is not used in the rinse routine of FIG. 10.

In block 1 of FIG. 14, the supply valve 27 is closed and the mixing pump 25 is operated to recirculate fluid in the mixing vessel 17. Then the cell is tilted by operating the motor 50 to lower the cell until the cam surface 52 engages the pin 53 and causes the cell to rotate about the pivot axis 54. Referring to FIG. 3, the position of the cell mounting block 48 as it engages the pin 53 is shown in broken lines at 48a. The fully lowered and tilted position of the mounting block is shown in dashed lines at 48b. The corresponding position of the platform 74 at it lowest position is shown at 74b. Tilting the cell to an angle of 45–60 degrees is generally sufficient for draining, although the cell can be tilted to about 90 degrees.

The waste valve 29 is opened to connect the pump 25 to waste, and the air valve 37 is opened to connect the cell along line 38 to the mixing vessel 17 above the liquid level. The cell pump 35 is then operated at a medium speed in reverse to pump the cell contents out of the passageway 117 into the mixing vessel 17, from which the mixing pump 25 pumps the fluid to waste. After waiting a sufficient time for the system to drain all the existing liquid and any suspended sample, the computer closes the waste valve 29 and the air valve 37 and stops both pumps.

Returning now to block 2 of FIG. 10, after the desired suspending liquid is placed in the liquid supply reservoir 27, the supply valve 28 is opened and the mixing pump 25 operated to fill the mixing vessel. Then the valve 28 is closed and the liquid is recirculated for a time through the line 24. Then the cell pump 35 is operated rapidly in the forward direction (to pump out of the passageway 118) for a set rinse time with the cell still tilted. The air valve 37 is then opened and circulation continued through the line 38 for a set time, after which the cell pump is stopped and the air valve is closed. Blocks 1–6 of FIG. 10 are then repeated to drain and rinse the system twice more to assure that all residue of the previous suspension is removed.

Block 8 of FIG. 10 refers to the subroutine of FIG. 13 for draining and refilling the cell. In block 1 of FIG. 13, all valves are closed. Then the cell pump is operated at moderate speed in reverse, the cell is tilted, and the air valve 37 is opened. After passage of the cell drain time, the cell pump is stopped. Then the direction of the pump is changed to forward and the pump is operated slowly for a time sufficient to fill the cell with liquid (which at this stage of operation of the system is particle-free). Then the air valve 37 is closed and the cell operated in the forward direction at fast speed for about 10 seconds to flush the line 34 between the air valve and the mixing vessel 17.

Returning to FIG. 10, the effectiveness of the rinse operation is checked in blocks 9-14. This is accomplished by reading the x-ray intensity at each data acquisition cell position in accordance with the sequence of FIG. 16, and comparing the results with known values for particle-free liquid. Block 10 of FIG. 10 refers to the subroutine of FIG. 16.

READ X-RAY INTENSITY

Figure 16A:
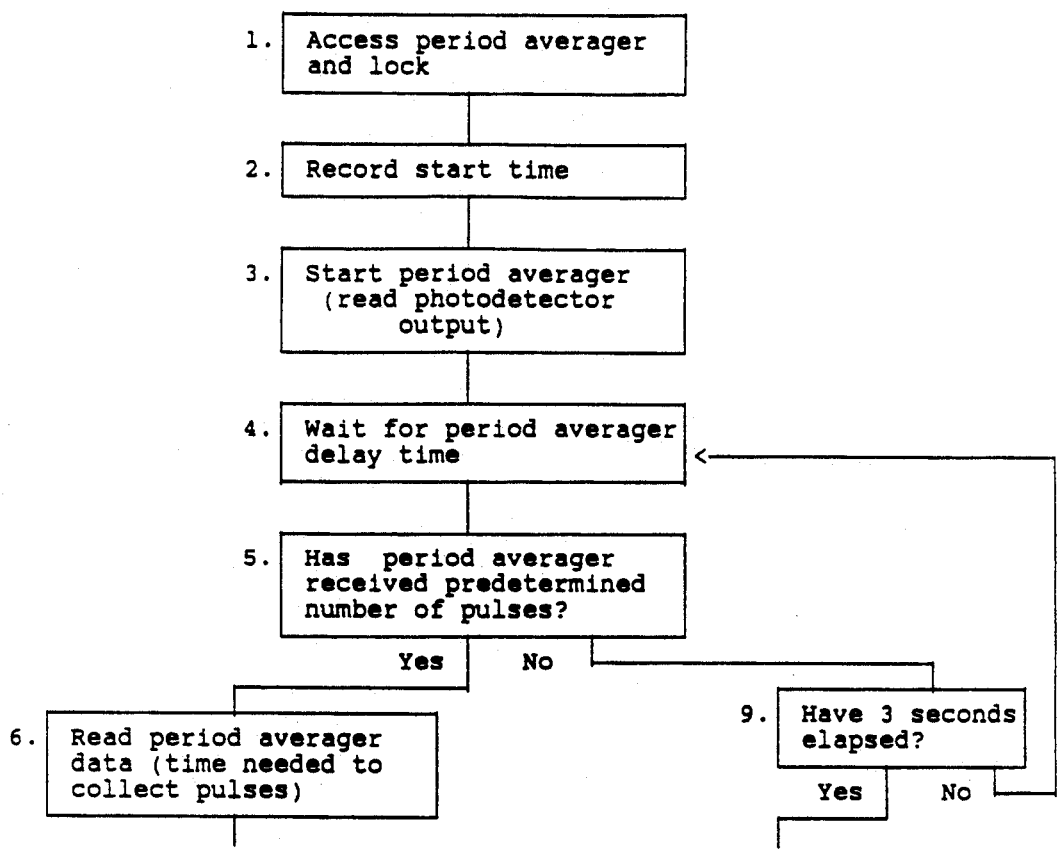
FIGS. 16A and 16B are a schematic flow diagram of the sequence for reading x-ray intensity utilized in operation of the present invention.
Figure 16B:
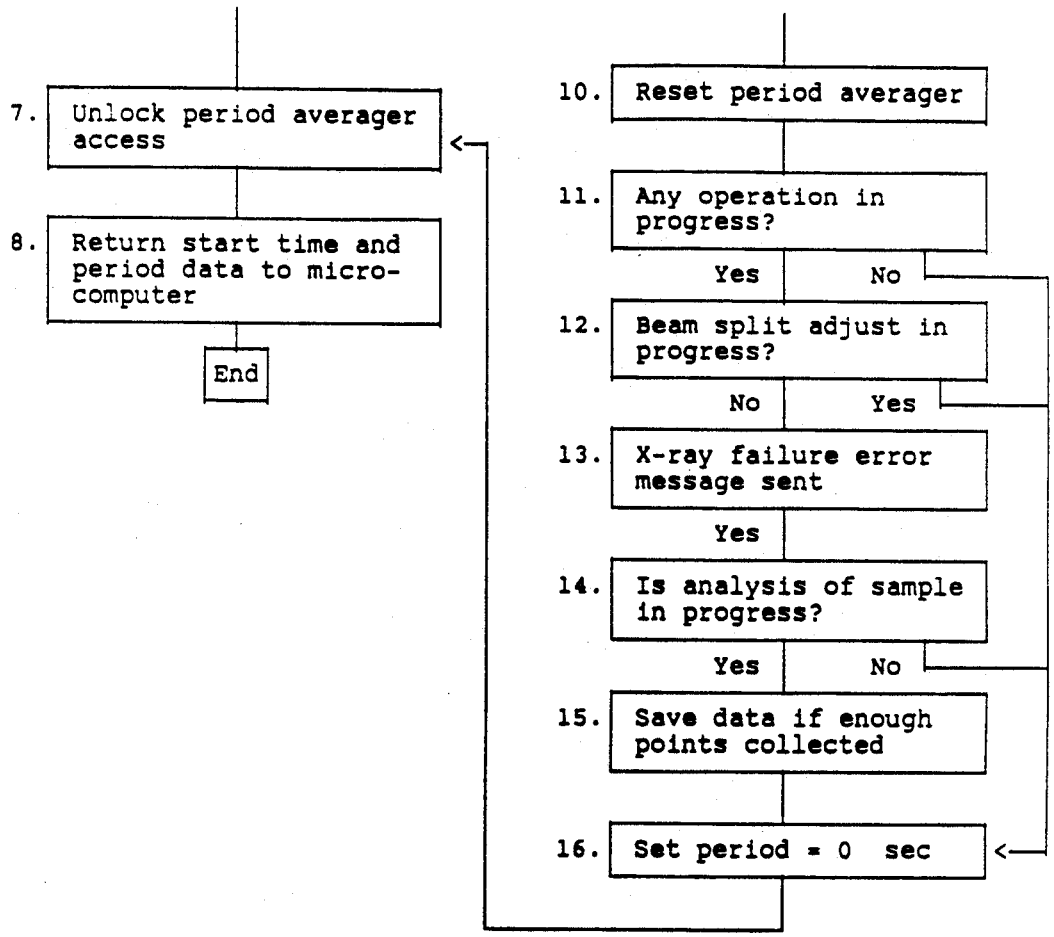

In block 1 of FIG. 16, the period averager 61 is accessed and locked in. It should be understood that the computer may be programmed for multi-tasking. Therefore, it is periodically necessary to access and lock into a system component before carrying out a task. The initial instruction to the period averager is to count a predetermined number of x-ray photons (such as 40,000 photons) and to report the time required for the photons to be counted, as described above. The computer checks the status of the period averager regularly (at intervals of a fraction of a second). If the status bit is set, the computer reads the period averager elapsed time data and the period averager is unlocked. If the status check indicates that the required pulses have not been counted, and more than 3 seconds have elapsed, the period averager is reset and checks are made in blocks 11-14 of FIG. 16 to determine whether other system operations are in progress that would prevent normal x-ray transmission.

At block 11 of FIG. 16, if no operation is in progress, the sequence moves to block 16, where the period averager time output is set at 0 seconds. The computer will recognize this arbitrary time as meaning no x-rays transmitted. Then the sequence goes to block 7 for unlocking of the period averager and return of data to the computer. If an operation is in progress, it is determined whether the operation is an adjustment of the beam split, which may temporarily block the x-ray slit. If so, the sequence proceeds to block 16. If the operation is not a beam split adjustment, an x-ray power failure message is displayed and a check is made to determine whether the operation is a sample run. If not, the sequence moves to block 16. If so, it is determined whether enough of the run has been completed to permit meaningful data reduction and presentation of particle size information. If so, the partial run data will be saved for later analysis.

After the computer reads the intensity data, the operation returns to FIG. 10 at block 11. The intensity is stored in association with the present calibrated cell position. In the above manner, x-ray intensity readings are obtained for each of the data acquisition cell positions until it is detected, in block 12 of FIG. 10, that the cell has reached the final such position adjacent to the beam split position. The data for each position is stored for comparison in block 13 with similar data previously obtained using the sequence shown in FIG. 12, described below. If the clarity of the liquid is acceptable after rinsing by comparison to the prior data, the pumps are turned off and the system returns to the operating sequence of FIG. 9. If clarity is not acceptable, the entire rinse routine of FIG. 10 is repeated, twice if necessary, and then an error message is displayed. Unsuccessful rinsing may indicate that deposits have caked upon the cell walls or windows and cannot be removed by fluid circulation.

BEAM SPLIT

Figure 11:
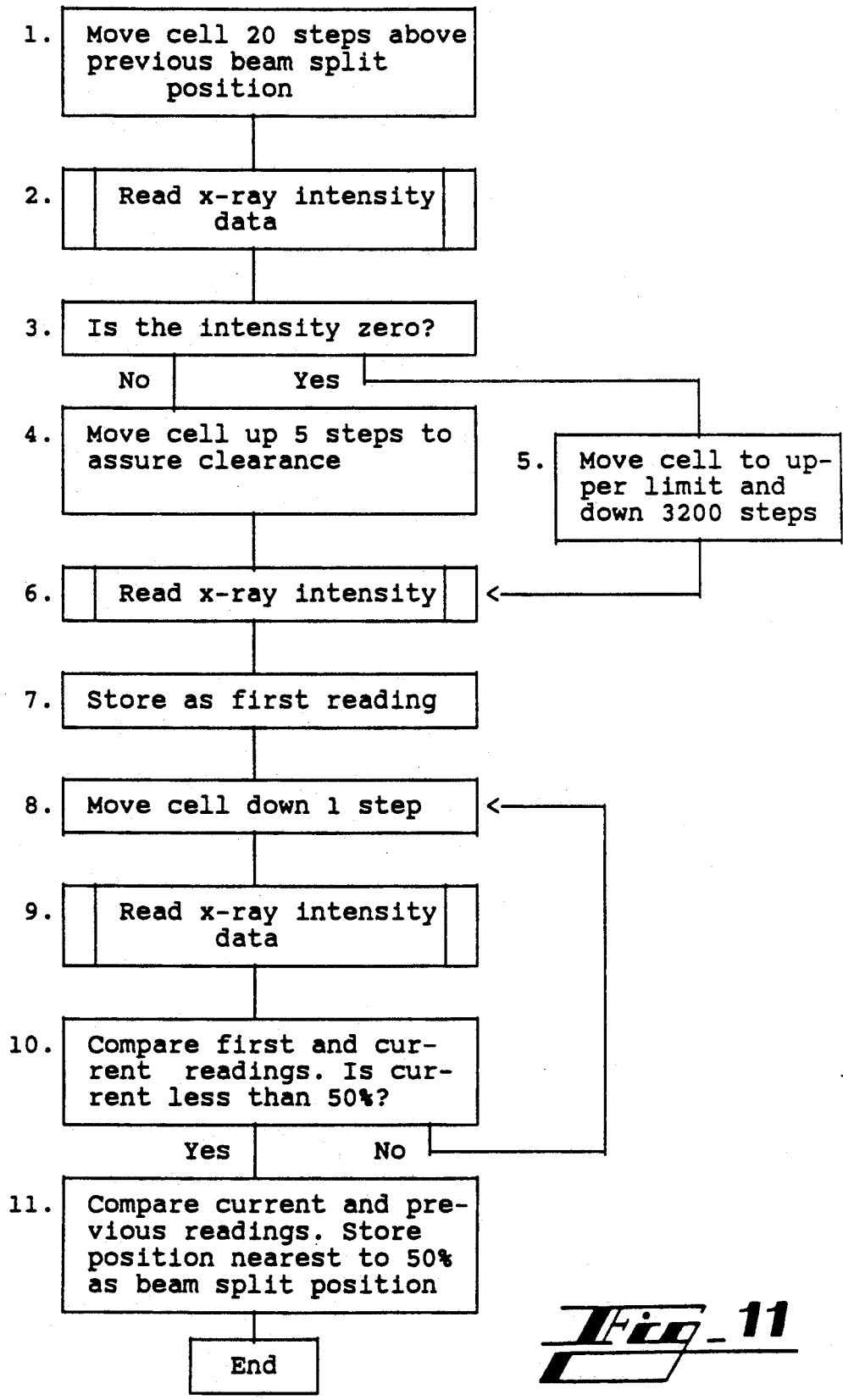
FIG. 11 is a schematic flow diagram of the sequence for determining the beam split utilized in operation of the present invention.

Returning now to block 3 of FIG. 9, the procedure for adjusting the recorded beam split position is charted in FIG. 11. The cell is first moved by operation of the motor 50 to a position 20 steps of the motor above the previously recorded beam split position. Then the x-ray intensity data at that position is read per the routine of FIG. 16 described above. At this position, the full intensity of the beam should pass through the cell. If, as expected, the intensity is not zero, the cell is moved up an additional 5 steps to assure that no partial obstruction of the beam by the top of the cell. However, if the intensity is zero, the cell is moved to its upper limit and then down 3200 steps to reestablish a known position with the beam passing through the cell.

In block 6 of FIG. 11, the x-ray intensity is again read to establish an initial reading which is stored. The cell is then moved down one step of the motor, and the x-ray intensity is again read. The initial and current intensities are compared, and it is determined whether the current reading is less than 50% of the initial intensity. If not, the cell is again moved down one step and a new intensity reading is compared to the initial reading. When the cell has been moved far enough down to obtain a 50% comparison, the current and next previous intensity readings are compared. The cell position of the reading closest to 50% of the initial intensity is stored as the beam split position of the cell 15.

CALIBRATE $I_o$ AND DETECT BUBBLES

Figure 12:
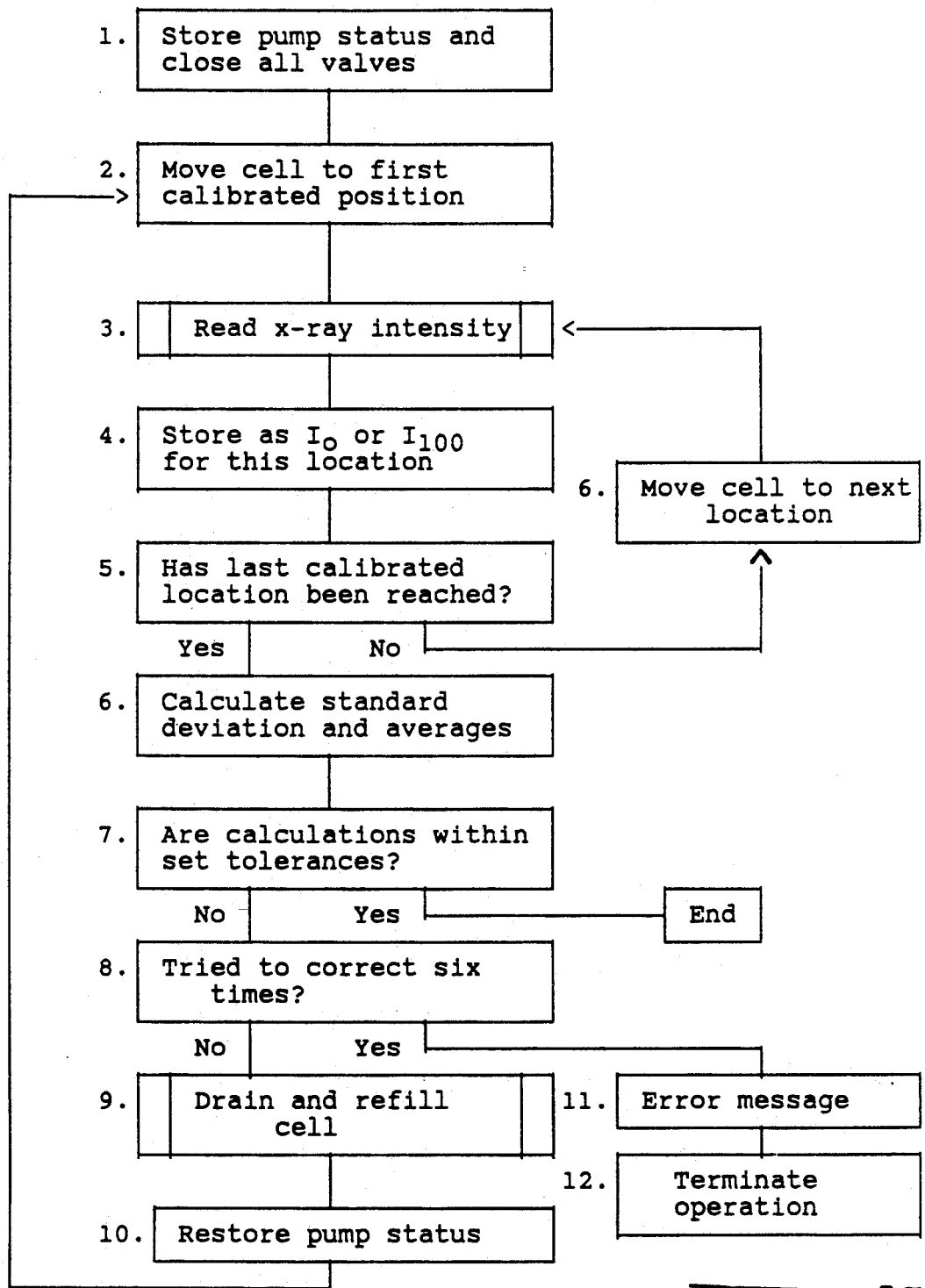
FIG. 12 is a schematic flow diagram of the sequence for detecting bubbles and determining cell transmitted intensity data utilized in operation of the present invention.

Returning to block 4 of FIG. 9, the routine for calibrating the selected cell positions by obtaining $I_o$ baseline data is charted in FIG. 12. This is a general routine for scanning the selected cell positions to obtain transmitted intensity data used to calibrate the cell positions for either $I_o$ or $I_{100}$ data, depending on whether sample is suspended in the liquid, and to indicate whether bubbles are present in the cell. At this point in the operation of the system, no sample has been introduced into the suspending liquid, so the scan will determine the $I_o$ data.

First, the pumps 25 and 35 are stopped and all valves are closed. Then the cell is moved to the first selected data acquisition position. In the preferred embodiment, 220 positions between the beam split position and a position one inch above beam split are arbitrarily selected as the only points at which sample data may be taken. An important feature of the analyzer 10 is the concept of calibrating the cell at each of these positions rather than accepting average or overall values for $I_o$ and $I_{100}$.

At the first such position, preferably one inch from beam split, the x-ray transmitted intensity is read according to FIG. 16, and the data is stored as $I_o$ for that position. This is repeated for all of the selected data acquisition positions of the cell. Then the standard deviation and average of the measured values are analyzed for uniformity. If they fall within predetermined tolerances, the apparatus may proceed to analysis. If the tolerances are not met, corrective action is taken in the form of draining and refilling the cell by executing the routine of FIG. 13, described above, to drive out any bubbles that may be responsible for the non-uniformity. Then the scanning is begun again (block 2) at the first location and new data collected for all the locations. If the values still do not meet the tolerances the corrective action is repeated for a total of six scans. If still unacceptable, the operation of the apparatus is terminated and an error message is displayed.

The scanning data thus is used to detect problems, such as the presence of a bubble, the presence of sample not rinsed out after a previous run, or a change in some other characteristic of the cell that should be investigated. Another test that may be carried out is to compare the average data for the top 5% of the cell to the bottom 95% of the cell, since bubbles often migrate to the top of the cell.

DRAIN AND LOAD SAMPLE

Returning to block 5 of FIG. 9, the system is now ready to receive the sample, which is manually deposited into the mixing vessel 17. Some samples must be pre-dispersed in suspending liquid, while others disperse easily and may be placed into the mixing vessel in powder form to be mixed with suspending liquid already present. It should be understood that an autosampling device could be connected to the mixing vessel or to the lines 33 and 34 to supply the system with a number of samples in sequence for analysis without operator attention.

The routine for draining the system and loading the sample into the cell is charted in FIG. 14. The sequence for draining the cell in blocks 1-4 of FIG. 14 was described above in connection with rinsing the cell. It should be noted that it is not always necessary to drain the mixing vessel to waste. For example, particle-free liquid in the cell may be drained to the mixing vessel but not discarded if the sample to be loaded can be placed into the mixing vessel as a powder.

At block 5, the system accepts an operator instruction to load a sample. The mixer pump 25 is operated to thoroughly recirculate the suspended sample. Then the air valve 37 is opened and the cell pump 35 is operated at slow speed, forward direction for the predetermined cell fill time, so that the cell fills through the channel 122. The air valve is then closed and the cell pump is operated at fast speed in the forward direction for about 10 seconds to purge the line 34. The cell pump 35 is then reversed and operated at a fast speed to recirculate the suspension and maintain the sample within the cell in a fully suspended condition. At this point the concentration is checked according to the routine charted in FIG. 18.

In accordance with FIG. 18, the cell is moved to the highest data acquisition position, one inch above beam split. Raising the cell automatically restores the cell to an upright position. Then the x-ray intensity is read in accordance with FIG. 16. If the intensity is not within an acceptable range compared to the intensity measured previously through particle-free suspending liquid, a warning message will be displayed. The acceptable range is selected to prevent analysis of samples that are too concentrated or too dilute to produce good results based on the experience of those skilled in the art. If the intensity is not acceptable, the operator may dilute the sample or add more sample to the mixing vessel 17. A "high" or "low" concentration error message is displayed as appropriate.

CALIBRATE $I_{100}$

Returning now to FIG. 9, blocks 6-8 relate to further calibration of the data acquisition cell positions to determine $I_{100}$ for each such position. According to block 6, the suspension is recirculated through the cell by operation of the cell pump in reverse and the mixing pump, to thoroughly disperse the sample. The beam split position is again adjusted in accordance with FIG. 11, after which $I_{100}$ is measured for all 220 data acquisition positions according to the routine of FIG. 12, described above. As noted above, FIG. 12 provides $I_{100}$ data at this stage of the operation because the sample is fully suspended. The bubble detection and elimination aspects of FIG. 12 are also executed.

Following the $I_{100}$ calibration, the temperature sensor 62 signal is checked in block 10 of FIG. 9 to determine whether the temperature is within 0.5 degrees of the desired temperature set by the operator. If not, the temperature is rechecked after waiting periods until it becomes stable, unless the operator has bypassed the stabilization routine. Then the liquid density and viscosity values input earlier by the operator are interpolated according to the temperature in the cell environment.

PREPROGRAMMING RUN

Figure 15A:
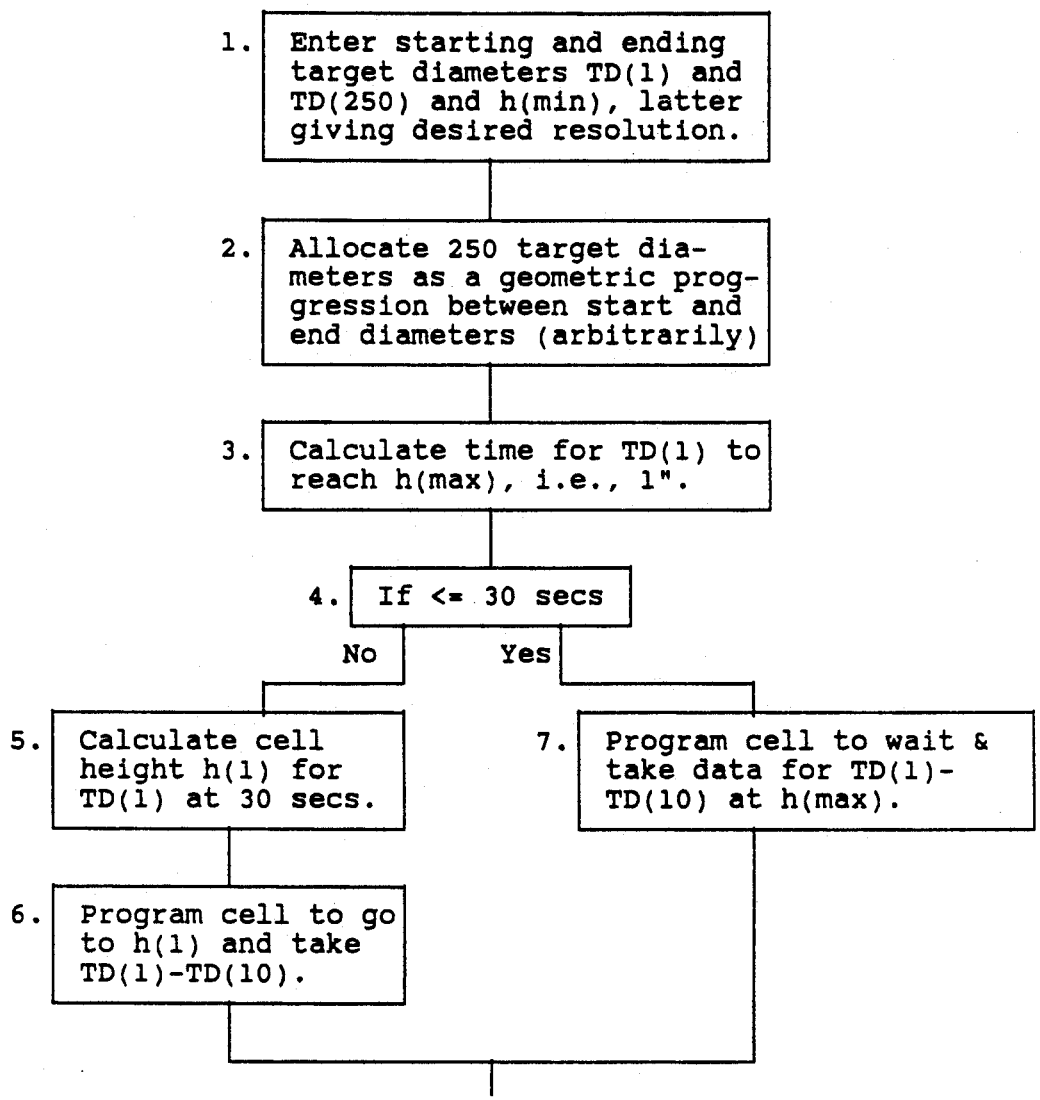
FIGS. 15A and 15B are a schematic flow diagram of the preprogramming sequence carried out prior to a run during operation of the present invention.
Figure 15B:
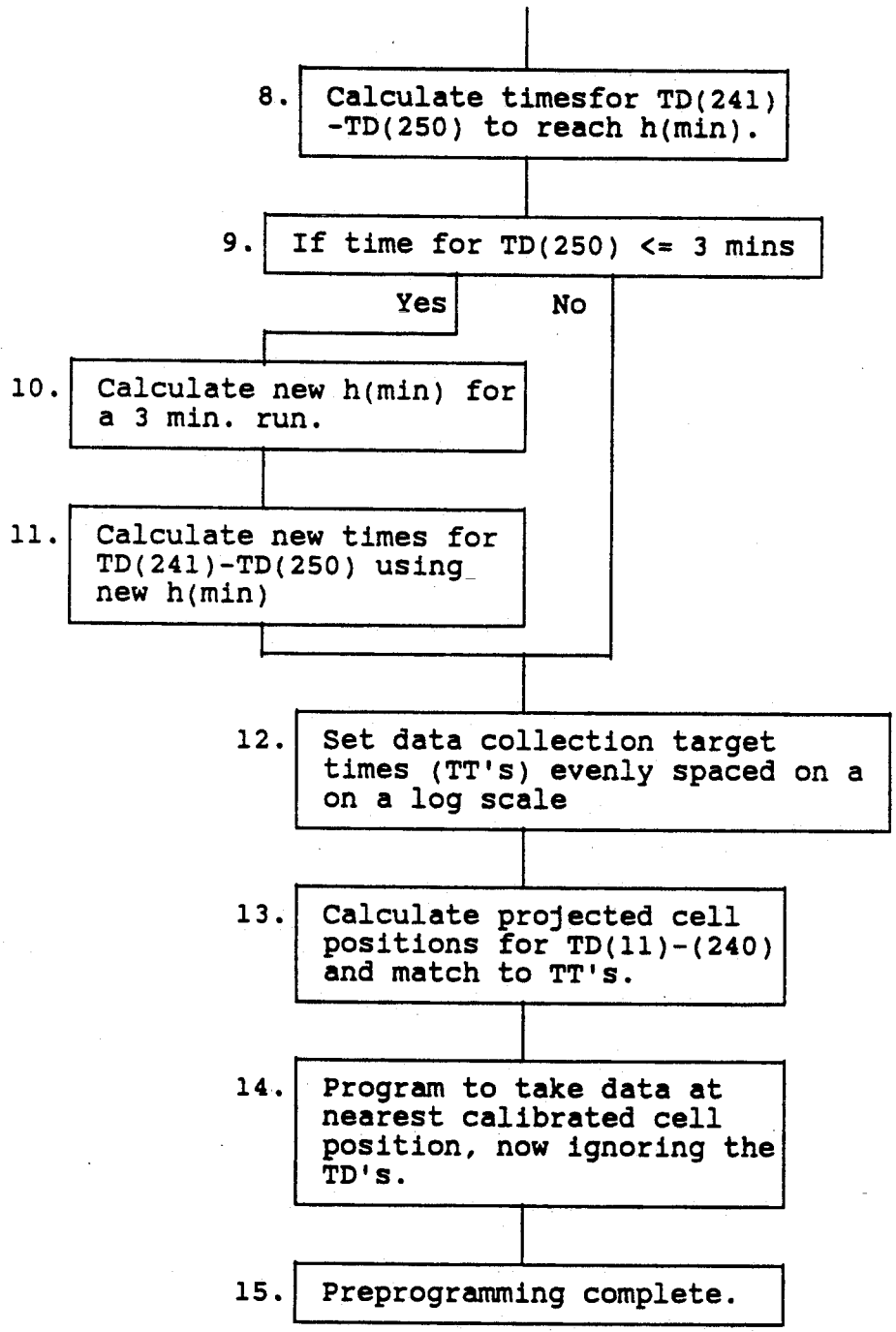

The computer now uses the appropriate data to "preprogram" the analysis using the procedure charted in FIG. 15. The purpose of this routine is to predetermine and calculate how the analysis will proceed by determining the precise times and data acquisition cell locations at which data points will be taken for the sample in question. The preprogramming of the run replaces the calculations and setting of rate switches done manually by the operator in prior analyzers.

Referring to FIG. 15, the operator must enter the largest and smallest particle diameters of interest in this run if not entered earlier. They must differ by at least a factor of 10; for example, if the largest "target diameter" (TD) is 10 microns, the analysis must proceed down to 1 micron or smaller. The operator must also input a desired value ($h_{min}$) for the closest approach of the x-ray beam to the top of the cell. A closer approach allows the run to be completed more quickly, but at lower resolution. The present analyzer 10 is able to acquire accurate data very close to the top of the cell, partly because of its ability to efficiently detect and eliminate bubbles which tend to migrate to the top of the cell, and also because it can provide complete suspension of the sample near the top of the cell prior to analysis.

Given the largest and smallest "target diameters" the computer allocates between them an additional 248 target diameters for a total of 250, TD(1)-TD(250). The largest diameter is referred to as TD(1), and the allocation is an arbitrary geometric progression between TD(1) and TD(250). The precise distribution of target diameters is not critical.

Each run is laid out so that the first ten data points are taken at a cell position (also referred to as cell height) one inch from the top of the cell ($h_{max}$) or at a lower cell position if it will take too long for TD(1) to reach $h_{max}$. Thus in block 3 of FIG. 15 the time for TD(1) to settle from the top of the cell to $h_{max}$ is calculated. If this time is less than 30 seconds, data for the first ten target diameters will be taken at $h_{max}$. If the time exceeds 30 seconds, the cell position that will be reached by TD(1) in 30 seconds is calculated and data for the first ten diameters will be taken at this calculated cell position ($h_1$). However, $h_1$ will never be permitted to be less than $h_{min}$. The run is also structured so that the last ten data points are taken at $h_{min}$, but the minimum length of a run is set at 3 minutes. Therefore, in block 8 the times for TD(241)-TD(250) to reach $h_{min}$ are calculated, and if the time for TD(250) is less than 3 minutes, a new $h_{min}$ is set for a 3 minute run (but never higher than $h_{max}$), and the times for TD(241)-TD(250) to reach the new $h_{min}$ are calculated.

Stokes' Law provides that particles of a certain diameter will have settled a certain distance at a certain time. Measuring the x-ray intensity at the time and distance will give information concerning particles of the particular size. It is possible to know in advance of the actual run exactly where and when data will be taken and the diameter to which the data will be relevant. In block 12 of FIG. 15, target times (TT's) for data collection are arbitrarily set, spaced evenly on a log scale. Then a projected cell position is calculated for each target diameter so as to take data at one of the target times.

For those calculated positions that do not match one of the precalibrated data acquisition cell positions, the run is programmed to take data at the nearest calibrated position and at the designated time. Thus, such data will not relate to one of the assigned target diameters. However, the actual diameter will be calculated from Stokes' Law using the other parameters. Although not critical to the accuracy of each point, the time distribution along a log scale is maintained in order to ensure a relatively even distribution of data points during a run. Of course, the data acquisition positions are not altered after they are calibrated, and therefore the target diameters must be altered to fit the given time and position values. Those skilled in the art will understand that preference could be given to target diameter in place of one of the other parameters.

CONDUCT ANALYSIS

Figure 17A:
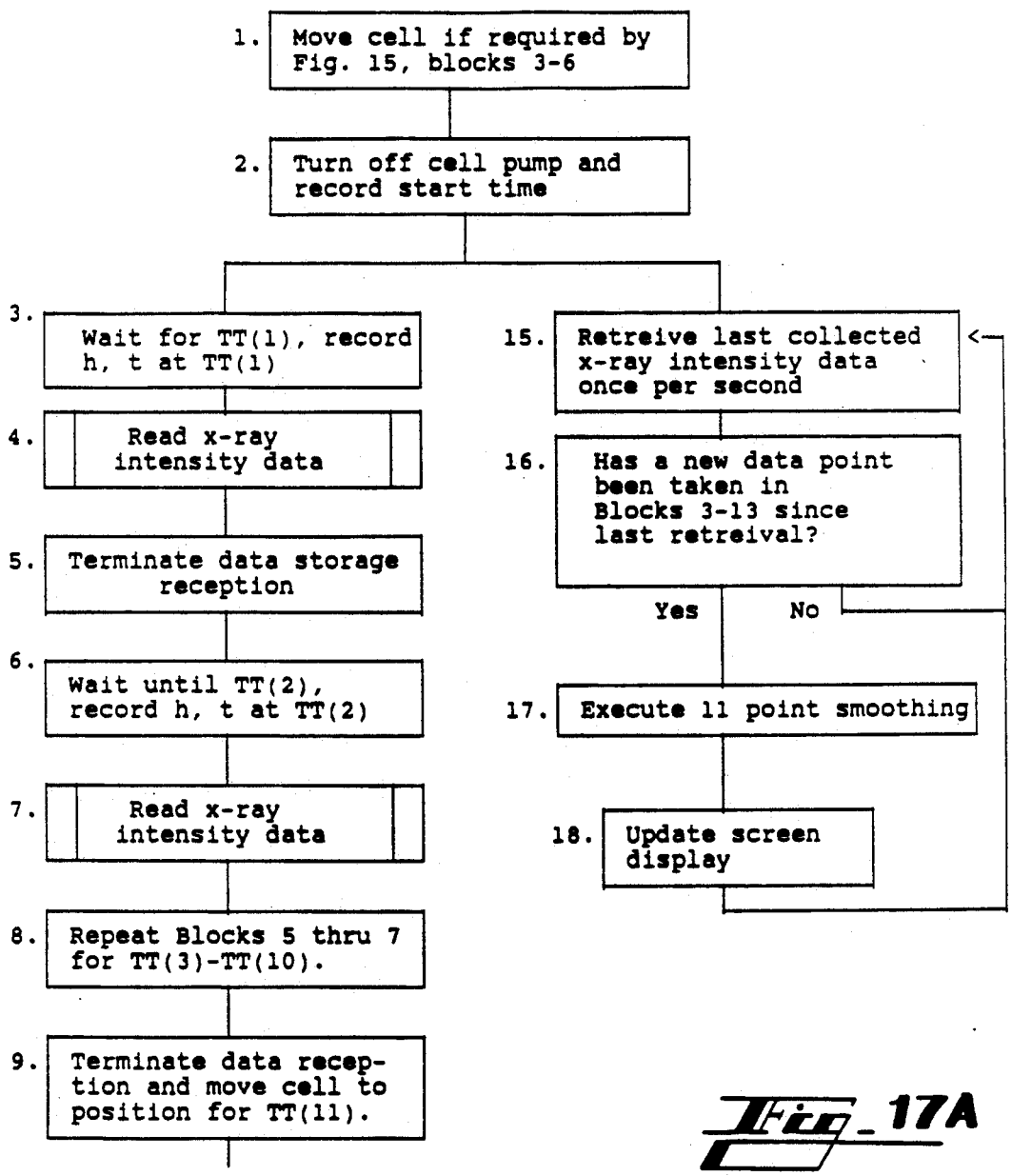

Block 13 of FIG. 9 refers to the routine of FIG. 17 for actually analyzing the sample. First, the cell is moved to $h_1$ if required by blocks 3-6 of the FIG. 15 preprogramming sequence. Then the cell pump is stopped to allow sedimentation to begin and the start time is stored. At target time TT(1), the cell position and time are stored and the x-ray intensity is read according to FIG. 16. At TT(2), the position, time and intensity are again stored, and this is repeated at least until after the taking of data at TT(10). If TT(11) is "mapped" against a cell position other than $h_1$, the cell is moved to that position and stopped while awaiting TT(11), at which time the intensity is read and stored with the position and time information.

Blocks 9-11 of FIG. 17 are then repeated to obtain data points for TT(12)-TT(240), moving the cell as required by the preprogramming routine. This will result in intermittent movement of the cell, and each movement will vary in distance, because not all of the calibrated data acquisition positions will be used in a particular run, and often the cell will remain stopped in one position while waiting for several target times. Prior to TT(241), the cell is moved to $h_{min}$ for the taking of data in the same way at TT(241)-TT(250).

Optionally, the data acquisition routine can be terminated after a selected percent finer has been reached.

While the data acquisition routine is progressing, the results of the analysis may also be presented on the computer screen, in accordance with blocks 15-18 of FIG. 17. The data from the main analysis run (blocks 3-13 of FIG. 17) is used. Once per second, the screen display routine checks to determine whether a new data point has been taken. If so, the intensity reading obtained is then processed using a conventional Savitsky-Golay eleven point smoothing routine to fit a curve with five prior and five subsequent readings and plotted for the screen display. The pixel on the screen on the fitted curve for the diameter in question is illuminated, and connected to the pixel for the previous data point by a straight line. Thus, each data point is added to the curve after five subsequent intensity readings have been obtained, and an approximation of the particle size distribution curve is shown on the screen as the analysis proceeds. Alternately, the screen plot can be interpolated using frequent independent intensity readings as well as the intermittent preprogrammed intensity readings.

As shown in FIG. 19, a digital display of the current x-ray intensity may also be shown and updated as the analysis proceeds. Separate and shared once per second intensity readings are obtained and smoothed using an eleven point smoothing routine as described above. Prior to sedimentation, this display indicates the status of the x-ray transmission and detection apparatus. During sedimentation, it gives the percent finer.

Returning to block 14 of FIG. 9, at the completion of data acquisition, the total run time is stored and the cell pump operated at full scale speed in a forward direction to dislodge sediment from the bottom of the cell. This pump speed can be selected according to the nature of the sample to be the slowest speed needed to keep the sample fully suspended. If a new sample or new suspending liquid, or both, are to be used for the next run, the system is rinsed according to the routine of FIG. 10. Alternately, the operator may request an immediate repeat analysis of the same sample.

The stored raw intensity data is smoothed, and the individual points interpolated using conventional cubic spline techniques, such as the Akima method, to provide smooth plots, using dot matrix printers or x-y plotters. Such plots may include, for example, cumulative mass percent finer (or coarser) vs. diameter, cumulative area percent finer (or coarser) vs. diameter, cumulative number percent finer (or coarser) vs. diameter and analogous histograms. Processed data can also be presented in tabular form.

It will be understood that repeat analyses or analyses of new samples using the same suspending liquid do not require complete repetition of the foregoing operations. For example, introducing a new sample into the same liquid does not require recalibration of the $I_o$ values for the cell, but does require reestablishing the $I_{100}$ values. Therefore, the cell can be rinsed, drained and loaded with the new sample according to appropriate steps of FIGS. 10 and 14, new sample data entered, the new run preprogrammed per FIG. 15, and new $I_{100}$ values obtained according to FIG. 12. Then the analysis can proceed as described above.

SAFETY INTERLOCK

Operation of the x-ray safety interlock will be apparent from the above description of its components.

Whenever the cell compartment door 130 is opened, the cam 146 allows the plunger 144 and rocker member 136 to move toward the door, raising the horizontal member 138 to a position over the slit 41. Only when the door 130 is again completely shut will x-rays be permitted to enter the cell compartment.

ALTERNATE CELL CONSTRUCTION

FIGS. 20 and 21 show an alternate embodiment 315 for the construction of the sample cell. The cell 315 is modified at the location at which the passageway 118, as shown in FIG. 5, enters the cell cavity 115. As shown diagrammatically in FIG. 20, a cell cavity 316 defined in a plate 300 (corresponding to the plate 100 of FIG. 5) communicates at the top of the cell cavity with a passage 330. A barrier 332 extends from the top of the passage 330 to a point spaced above the bottom of the passage 330. The barrier 332 extends horizontally across the entire cross section of the passage 330. The vertical side wall 317 of the cavity 316 extends upwardly to form a projection 334 which terminates at a point spaced below the top of the cell cavity 316 and partially blocks the passage 330. The effective width of x-rays passing horizontally through the cell cavity, that is, the width measured by the detector, is designated by the letter A in FIG. 20. The horizontal distance between the inner wall 317 of the cell cavity 316 and the barrier 332 is designated by the letter B. The height of the barrier 332 measured from the top of the passage 330 is designated by the letter C. The height of the same barrier 332 measured from the top of the cell cavity 316 is designated by the letter E. The distance from the projection 334 to the top of the cell cavity is designated by the letter D.

The purpose of the barrier 332 is to prevent density gradients that may form in the passage 330 from causing low density material to flow into the top of the cell cavity 316 during sedimentation. In order for the barrier to function effectively, the distance B must be less than A, that is, the extension of the top of the cell to the barrier 332 must be less than the effective x-ray width A. Preferably, B is less than 30 percent of A, so as to minimize the tendency of sedimentation under the dimension B from significantly affecting the analysis. Furthermore, C must be greater than or equal to D, so that as particles settling through the distance C reach the bottom of the barrier 332, particles of the same size have already passed the end of the projection 334. Finally, E must be greater than D, so that the barrier extends down farther from the top of the cell cavity than the end of the projection 334. It is preferable, but not required, that B be minimized, and that the distance between the end of the projection 334 and the bottom of the passage 330 be minimized. It is also preferable to minimize the horizontal run of the passage 330 to minimize the formation of density gradients. Lengthening the horizontal run of the passage 330 would require a lengthening of the downward extent of the barrier 332 to hold low density material outside the cell cavity.

As shown in FIG. 20, the top surface of the projection 334 is preferably bevelled, with the bevelled surface facing outside the cell cavity 316. This results in higher density particles settling from under the dimension B moving toward the passage 330 rather than into the cell cavity 316. Similarly, the bottom surface of the barrier 332 is bevelled, with the bevelled surface facing away from the cell cavity. This results in low density suspension forming under the barrier 332 flowing up into the passage 330, rather than toward the cell cavity 316.

FIG. 21, shows an example of a cell cavity construction embodying the concepts shown in FIG. 20. The passage 330 is constructed having a minimum horizontal run, by turning the passage 330 upward into a vertical configuration immediately on the outside of the barrier 332. The construction of the port communicating with the cell cavity 316 at the lower end of the cell cavity is similar to the construction shown in FIG. 5. A wall 320 extends from the top of the cell to divide off a vertical channel 322. The bottom 324 of the wall 320 is slanted to provide a channel segment which enters the bottom of the cell at an angle above the horizontal. Thus, any low density suspension forming under the bottom of the wall 320 will tend to rise into the channel 322, rather than into the cell cavity 316, where it could distort the position of the particles from that predicted by Stokes Law. It should be noted that the channel 322 could have any orientation ranging from the vertical orientation shown in FIG. 21 to any angle above the horizontal. It is important that the segment of the channel 322 actually communicating with the cell cavity 316 not have a significant upper surface or boundary 324 that is either horizontal or angled inwardly to permit low density suspension forming thereunder to flow into the cell cavity. Such a surface 324 having a length greater than 10 percent of the width of the cell cavity in which sedimentation takes place is considered significant.

While this invention has been described in detail with particular reference to preferred embodiments thereof, it will be understood that variations and modifications can be effected within the spirit and scope of the invention as described hereinbefore and as defined in the appended claims.

We claim:

1. A sample cell apparatus for use in a sedimentation particle size analyzer, comprising:
    a sample compartment; and
    a passageway extending away from said compartment, said passageway including a downwardly extending barrier, and said compartment including a projection extending upwardly to partially block said passageway inside said barrier, said barrier ending below the upper end of said projection.

2. The sample cell of claim 1, wherein said passageway extends horizontally and even with the top of said compartment from said projection to said barrier;
    said barrier having a height measured from the top of said compartment greater than the distance from the top of said compartment to the upper end of said projection; and said barrier having a height measured from the top of said passageway outside said barrier greater than or equal to the distance from the top of said compartment to the upper end of said projection; and wherein
    said compartment includes windows for allowing x-rays to pass through said compartment; the horizontal distance from said compartment to said barrier being less than the effective width of x-rays passing through said compartment.

3. A sample cell of claim 2, wherein said distance from said compartment to said barrier is less than 30 percent of the effective width of x-rays passing through said compartment.

4. The sample cell of claim 3, wherein said passageway comprises a first passageway and further comprising a second passageway approaching the side of said compartment opposite said first passageway from an angle above the horizontal, and communicating with said compartment at a passageway segment including substantially no horizontal or inwardly inclined upper boundary, such that said second passageway provides essentially no horizontal settling channel from which low density material can rise to the top of said compartment.

* * * * *